United States Patent
Takaishi et al.

(10) Patent No.: US 11,464,720 B2
(45) Date of Patent: Oct. 11, 2022

(54) TRPA1 ACTIVITY INHIBITOR

(71) Applicants: MANDOM CORPORATION, Osaka (JP); TAKASAGO INTERNATIONAL CORPORATION, Tokyo (JP)

(72) Inventors: Masayuki Takaishi, Osaka (JP); Fumitaka Fujita, Osaka (JP); Hironori Shimizu, Osaka (JP); Shu Sakuyama, Osaka (JP); Kenya Ishida, Hiratsuka (JP); Kenji Maruyama, Hiratsuka (JP)

(73) Assignees: MANDOM CORPORATION, Osaka (JP); TAKASAGO INTERNATIONAL CORPORATION, Tokyo (JP)

( * ) Notice: Subject to any disclaimer, the term of this patent is extended or adjusted under 35 U.S.C. 154(b) by 176 days.

(21) Appl. No.: 16/495,663

(22) PCT Filed: Mar. 13, 2018

(86) PCT No.: PCT/JP2018/009696
§ 371 (c)(1),
(2) Date: Sep. 19, 2019

(87) PCT Pub. No.: WO2018/180460
PCT Pub. Date: Oct. 4, 2018

(65) Prior Publication Data
US 2020/0022889 A1 Jan. 23, 2020

(30) Foreign Application Priority Data
Mar. 30, 2017 (JP) .............................. JP2017-068027

(51) Int. Cl.
| | | |
|---|---|---|
| *A61K 8/34* | (2006.01) | |
| *A61Q 5/00* | (2006.01) | |
| *A61Q 15/00* | (2006.01) | |
| *A61Q 19/00* | (2006.01) | |
| *C07G 99/00* | (2009.01) | |

(52) U.S. Cl.
CPC .................. *A61K 8/34* (2013.01); *A61Q 5/00* (2013.01); *A61Q 15/00* (2013.01); *A61Q 19/00* (2013.01); *C07G 17/00* (2013.01)

(58) Field of Classification Search
CPC ...................................................... A61K 8/34
See application file for complete search history.

(56) References Cited

U.S. PATENT DOCUMENTS

| | | | |
|---|---|---|---|
| 2010/0168251 A1 | 7/2010 | Warr et al. | |
| 2011/0306665 A1 | 12/2011 | Kobayashi et al. | |
| 2013/0315843 A1 * | 11/2013 | Haught .................... | A61Q 9/02 424/53 |

FOREIGN PATENT DOCUMENTS

| | | | |
|---|---|---|---|
| JP | 2008-79528 A | 4/2008 | |
| JP | 2009-82053 A | 4/2009 | |
| JP | 2009-225733 A | 10/2009 | |
| JP | 2010-155992 A | 7/2010 | |
| JP | 2012-62304 A * | 3/2012 | ............... A61K 8/49 |
| JP | 2013-79233 A * | 5/2013 | ............... A61K 8/97 |
| JP | 2014-65690 A | 4/2014 | |
| JP | 2014-177473 A | 9/2014 | |

OTHER PUBLICATIONS

Letizia et al., "Arbanol", Food and Chemical Toxicology, vol. 38, Supplement 3, 2000, s11-s12.*
Letizia. C. S et al., Arbanol, Food and Chemical Toxicology, vol. 38, Supplement 3, 2000, sII-sI2, cited in ISR.
Okamoto et al., "Development of preservatives for paraben-free," Fragrance Journal, vol. 39, No. 2, Feb. 15, 2011, pp. 22-29, cited in ISR.
International Search Report dated May 15, 2018, issued in counterpart International Application No. PCT/JP2018/009696 (2 pages).

* cited by examiner

*Primary Examiner* — Svetlana M Ivanova
(74) *Attorney, Agent, or Firm* — WHDA, LLP

(57) ABSTRACT

This TRPA1 activity inhibitor contains a compound represented by formula (I) wherein $R^1$, $R^2$, $R^3$ and $R^4$ each independently represent a hydrogen atom or a methyl group, and $R^5$, $R^6$, $R^7$ and $R^8$ each independently represent a hydrogen atom, a methyl group or —O—$R^9$—OH (in the formula, $R^9$ represents an alkylene group optionally having a substituent group), provided that at least one group of $R^5$, $R^6$, $R^7$ and $R^8$ is —O—$R^9$—OH.

(I)

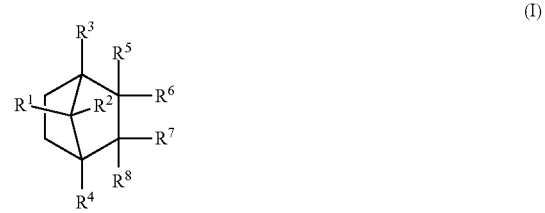

8 Claims, 2 Drawing Sheets

Specification includes a Sequence Listing.

SEQUENCE LISTING

```
<160> NUMBER OF SEQ ID NOS: 4

<210> SEQ ID NO 1
<211> LENGTH: 5190
<212> TYPE: DNA
<213> ORGANISM: Homo sapiens
<220> FEATURE:
<221> NAME/KEY: CDS
<222> LOCATION: (176)..(3535)

<400> SEQUENCE: 1
ccagaagttc tccagggctt ccgcagagcg acttttcgc tgcctgtgag ctgcagcgcg         60
ggagagctcg ggctcgcgcg acccccagcg cctggcaggc tgacagcgct ctctcgcccc       120
aggtgcccgc gcgcgtggtg agcagctgca ccaggtggcg tccggggtgg ggtca atg       178
                                                                Met
                                                                 1 aag cgc agc ctg agg aag atg tgg cgc cct gga gaa aag aag gag ccc        226
Lys Arg Ser Leu Arg Lys Met Trp Arg Pro Gly Glu Lys Lys Glu Pro
              5                  10                  15 cag ggc gtt gtc tat gag gat gtg ccg gac gac acg gag gat ttc aag        274
Gln Gly Val Val Tyr Glu Asp Val Pro Asp Asp Thr Glu Asp Phe Lys
```

-continued

|  | 20 |  |  |  | 25 |  |  |  | 30 |  |  |  |  |
|---|---|---|---|---|---|---|---|---|---|---|---|---|---|

```
gaa tcg ctt aag gtg gtt ttt gaa gga agt gca tat gga tta caa aac       322
Glu Ser Leu Lys Val Val Phe Glu Gly Ser Ala Tyr Gly Leu Gln Asn
     35                  40                  45 ttt aat aag caa aag aaa tta aaa aga tgt gac gat atg gac acc ttc       370
Phe Asn Lys Gln Lys Lys Leu Lys Arg Cys Asp Asp Met Asp Thr Phe
 50                  55                  60                  65 ttc ttg cat tat gct gca gca gaa ggc caa att gag cta atg gag aag       418
Phe Leu His Tyr Ala Ala Ala Glu Gly Gln Ile Glu Leu Met Glu Lys
                     70                  75                  80 atc acc aga gat tcc tct ttg gaa gtg ctg cat gaa atg gat gat tat       466
Ile Thr Arg Asp Ser Ser Leu Glu Val Leu His Glu Met Asp Asp Tyr
                 85                  90                  95 gga aat acc cct ctg cat tgt gct gta gaa aaa aac caa att gaa agc       514
Gly Asn Thr Pro Leu His Cys Ala Val Glu Lys Asn Gln Ile Glu Ser
             100                 105                 110 gtt aag ttt ctt ctc agc aga gga gca aac cca aat ctc cga aac ttc       562
Val Lys Phe Leu Leu Ser Arg Gly Ala Asn Pro Asn Leu Arg Asn Phe
         115                 120                 125 aac atg atg gct cct ctc cac ata gct gtg cag ggc atg aat aat gag       610
Asn Met Met Ala Pro Leu His Ile Ala Val Gln Gly Met Asn Asn Glu
130                 135                 140                 145 gtg atg aag gtc ttg ctt gag cat aga act att gat gtt aat ttg gaa       658
Val Met Lys Val Leu Leu Glu His Arg Thr Ile Asp Val Asn Leu Glu
                150                 155                 160 gga gaa aat gga aac aca gct gtg atc att gcg tgc acc aca aat aat       706
Gly Glu Asn Gly Asn Thr Ala Val Ile Ile Ala Cys Thr Thr Asn Asn
            165                 170                 175 agc gaa gca ttg cag att ttg ctt aaa aaa gga gct aag cca tgt aaa       754
Ser Glu Ala Leu Gln Ile Leu Leu Lys Lys Gly Ala Lys Pro Cys Lys
        180                 185                 190 tca aat aaa tgg gga tgt ttc cct att cac caa gct gca ttt tca ggt       802
Ser Asn Lys Trp Gly Cys Phe Pro Ile His Gln Ala Ala Phe Ser Gly
    195                 200                 205 tcc aaa gaa tgc atg gaa ata ata cta agg ttt ggt gaa gag cat ggg       850
Ser Lys Glu Cys Met Glu Ile Ile Leu Arg Phe Gly Glu Glu His Gly
210                 215                 220                 225 tac agt aga cag ttg cac att aac ttt atg aat aat ggg aaa gcc acc       898
Tyr Ser Arg Gln Leu His Ile Asn Phe Met Asn Asn Gly Lys Ala Thr
                230                 235                 240 cct ctc cac ctg gct gtg caa aat ggt gac ttg gaa atg atc aaa atg       946
Pro Leu His Leu Ala Val Gln Asn Gly Asp Leu Glu Met Ile Lys Met
            245                 250                 255 tgc ctg gac aat ggt gca caa ata gac cca gtg gag aag gga agg tgc       994
Cys Leu Asp Asn Gly Ala Gln Ile Asp Pro Val Glu Lys Gly Arg Cys
        260                 265                 270 aca gcc att cat ttt gct gcc acc cag gga gcc act gag att gtt aaa      1042
Thr Ala Ile His Phe Ala Ala Thr Gln Gly Ala Thr Glu Ile Val Lys
    275                 280                 285 ctg atg ata tcg tcc tat tct ggt agc gtg gat att gtt aac aca acc      1090
Leu Met Ile Ser Ser Tyr Ser Gly Ser Val Asp Ile Val Asn Thr Thr
290                 295                 300                 305 gat gga tgt cat gag acc atg ctt cac aga gct tca ttg ttt gat cac      1138
Asp Gly Cys His Glu Thr Met Leu His Arg Ala Ser Leu Phe Asp His
                310                 315                 320 cat gag cta gca gac tat tta att tca gtg gga gca gat att aat aag      1186
His Glu Leu Ala Asp Tyr Leu Ile Ser Val Gly Ala Asp Ile Asn Lys
            325                 330                 335 atc gat tct gaa gga cgc tct cca ctt ata tta gca act gct tct gca      1234
```

|     |     |     |     |     |     |     |     |     |     |     |     |      |
|-----|-----|-----|-----|-----|-----|-----|-----|-----|-----|-----|-----|------|
| Ile | Asp | Ser | Glu | Gly | Arg | Ser | Pro | Leu | Ile | Leu | Ala | Thr Ala Ser Ala |
|     |     |     | 340 |     |     |     | 345 |     |     |     | 350 |      |

```
tct tgg aat att gta aat ttg cta ctc tct aaa ggt gcc caa gta gac    1282
Ser Trp Asn Ile Val Asn Leu Leu Leu Ser Lys Gly Ala Gln Val Asp
        355                 360                 365 ata aaa gat aat ttt gga cgt aat ttt ctg cat tta act gta cag caa    1330
Ile Lys Asp Asn Phe Gly Arg Asn Phe Leu His Leu Thr Val Gln Gln
370                 375                 380                 385 cct tat gga tta aaa aat ctg cga cct gaa ttt atg cag atg caa cag    1378
Pro Tyr Gly Leu Lys Asn Leu Arg Pro Glu Phe Met Gln Met Gln Gln
                390                 395                 400 atc aaa gag ctg gta atg gat gaa gac aac gat ggg tgt act cct cta    1426
Ile Lys Glu Leu Val Met Asp Glu Asp Asn Asp Gly Cys Thr Pro Leu
            405                 410                 415 cat tat gca tgt aga cag ggg ggc cct ggt tct gta aat aac cta ctt    1474
His Tyr Ala Cys Arg Gln Gly Gly Pro Gly Ser Val Asn Asn Leu Leu
                420                 425                 430 ggc ttt aat gtg tcc att cat tcc aaa agc aaa gat aag aaa tca cct    1522
Gly Phe Asn Val Ser Ile His Ser Lys Ser Lys Asp Lys Lys Ser Pro
435                 440                 445 ctg cat ttt gca gcc agt tat ggg cgt atc aat acc tgt cag agg ctc    1570
Leu His Phe Ala Ala Ser Tyr Gly Arg Ile Asn Thr Cys Gln Arg Leu
450                 455                 460                 465 cta caa gac ata agt gat acg agg ctt ctg aat gaa ggt gac ctt cat    1618
Leu Gln Asp Ile Ser Asp Thr Arg Leu Leu Asn Glu Gly Asp Leu His
                470                 475                 480 gga atg act cct ctc cat ctg gca gca aag aat gga cat gat aaa gta    1666
Gly Met Thr Pro Leu His Leu Ala Ala Lys Asn Gly His Asp Lys Val
                485                 490                 495 gtt cag ctt ctt ctg aaa aaa ggt gca ttg ttt ctc agt gac cac aat    1714
Val Gln Leu Leu Leu Lys Lys Gly Ala Leu Phe Leu Ser Asp His Asn
            500                 505                 510 ggc tgg aca gct ttg cat cat gcg tcc atg ggc ggg tac act cag acc    1762
Gly Trp Thr Ala Leu His His Ala Ser Met Gly Gly Tyr Thr Gln Thr
515                 520                 525 atg aag gtc att ctt gat act aat ttg aag tgc aca gat cgc ctg gat    1810
Met Lys Val Ile Leu Asp Thr Asn Leu Lys Cys Thr Asp Arg Leu Asp
530                 535                 540                 545 gaa gac ggg aac act gca ctt cac ttt gct gca agg gaa ggc cac gcc    1858
Glu Asp Gly Asn Thr Ala Leu His Phe Ala Ala Arg Glu Gly His Ala
                550                 555                 560 aaa gcc gtt gcg ctt ctt ctg agc cac aat gct gac ata gtc ctg aac    1906
Lys Ala Val Ala Leu Leu Leu Ser His Asn Ala Asp Ile Val Leu Asn
                565                 570                 575 aag cag cag gcc tcc ttt ttg cac ctt gca ctt cac aat aag agg aag    1954
Lys Gln Gln Ala Ser Phe Leu His Leu Ala Leu His Asn Lys Arg Lys
            580                 585                 590 gag gtt gtt ctt acg atc atc agg agc aaa aga tgg gat gaa tgt ctt    2002
Glu Val Val Leu Thr Ile Ile Arg Ser Lys Arg Trp Asp Glu Cys Leu
595                 600                 605 aag att ttc agt cat aat tct cca ggc aat aaa tgt cca att aca gaa    2050
Lys Ile Phe Ser His Asn Ser Pro Gly Asn Lys Cys Pro Ile Thr Glu
610                 615                 620                 625 atg ata gaa tac ctc cct gaa tgc atg aag gta ctt tta gat ttc tgc    2098
Met Ile Glu Tyr Leu Pro Glu Cys Met Lys Val Leu Leu Asp Phe Cys
                630                 635                 640 atg ttg cat tcc aca gaa gac aag tcc tgc cga gac tat tat atc gag    2146
Met Leu His Ser Thr Glu Asp Lys Ser Cys Arg Asp Tyr Tyr Ile Glu
            645                 650                 655
```

```
tat aat ttc aaa tat ctt caa tgt cca tta gaa ttc acc aaa aaa aca      2194
Tyr Asn Phe Lys Tyr Leu Gln Cys Pro Leu Glu Phe Thr Lys Lys Thr
            660                 665                 670 cct aca cag gat gtt ata tat gaa ccg ctt aca gcc ctc aac gca atg      2242
Pro Thr Gln Asp Val Ile Tyr Glu Pro Leu Thr Ala Leu Asn Ala Met
    675                 680                 685 gta caa aat aac cgc ata gag ctt ctc aat cat cct gtg tgt aaa gaa      2290
Val Gln Asn Asn Arg Ile Glu Leu Leu Asn His Pro Val Cys Lys Glu
690                 695                 700                 705 tat tta ctc atg aaa tgg ttg gct tat gga ttt aga gct cat atg atg      2338
Tyr Leu Leu Met Lys Trp Leu Ala Tyr Gly Phe Arg Ala His Met Met
                710                 715                 720 aat tta gga tct tac tgt ctt ggt ctc ata cct atg acc att ctc gtt      2386
Asn Leu Gly Ser Tyr Cys Leu Gly Leu Ile Pro Met Thr Ile Leu Val
        725                 730                 735 gtc aat ata aaa cca gga atg gct ttc aac tca act ggc atc atc aat      2434
Val Asn Ile Lys Pro Gly Met Ala Phe Asn Ser Thr Gly Ile Ile Asn
            740                 745                 750 gaa act agt gat cat tca gaa ata cta gat acc acg aat tca tat cta      2482
Glu Thr Ser Asp His Ser Glu Ile Leu Asp Thr Thr Asn Ser Tyr Leu
    755                 760                 765 ata aaa act tgt atg att tta gtg ttt tta tca agt ata ttt ggg tat      2530
Ile Lys Thr Cys Met Ile Leu Val Phe Leu Ser Ser Ile Phe Gly Tyr
770                 775                 780                 785 tgc aaa gaa gcg ggg caa att ttc caa cag aaa agg aat tat ttt atg      2578
Cys Lys Glu Ala Gly Gln Ile Phe Gln Gln Lys Arg Asn Tyr Phe Met
                790                 795                 800 gat ata agc aat gtt ctt gaa tgg att atc tac acg acg ggc atc att      2626
Asp Ile Ser Asn Val Leu Glu Trp Ile Ile Tyr Thr Thr Gly Ile Ile
        805                 810                 815 ttt gtg ctg ccc ttg ttt gtt gaa ata cca gct cat ctg cag tgg caa      2674
Phe Val Leu Pro Leu Phe Val Glu Ile Pro Ala His Leu Gln Trp Gln
            820                 825                 830 tgt gga gca att gct gtt tac ttc tat tgg atg aat ttc tta ttg tat      2722
Cys Gly Ala Ile Ala Val Tyr Phe Tyr Trp Met Asn Phe Leu Leu Tyr
    835                 840                 845 ctt caa aga ttt gaa aat tgt gga att ttt att gtt atg ttg gag gta      2770
Leu Gln Arg Phe Glu Asn Cys Gly Ile Phe Ile Val Met Leu Glu Val
850                 855                 860                 865 att ttg aaa act ttg ttg agg tct aca gtt gta ttt atc ttc ctt ctt      2818
Ile Leu Lys Thr Leu Leu Arg Ser Thr Val Val Phe Ile Phe Leu Leu
                870                 875                 880 ctg gct ttt gga ctc agc ttt tac atc ctc ctg aat tta cag gat ccc      2866
Leu Ala Phe Gly Leu Ser Phe Tyr Ile Leu Leu Asn Leu Gln Asp Pro
        885                 890                 895 ttc agc tct cca ttg ctt tct ata atc cag acc ttc agc atg atg cta      2914
Phe Ser Ser Pro Leu Leu Ser Ile Ile Gln Thr Phe Ser Met Met Leu
            900                 905                 910 gga gat atc aat tat cga gag tcc ttc cta gaa cca tat ctg aga aat      2962
Gly Asp Ile Asn Tyr Arg Glu Ser Phe Leu Glu Pro Tyr Leu Arg Asn
    915                 920                 925 gaa ttg gca cat cca gtt ctg tcc ttt gca caa ctt gtt tcc ttc aca      3010
Glu Leu Ala His Pro Val Leu Ser Phe Ala Gln Leu Val Ser Phe Thr
930                 935                 940                 945 ata ttt gtc cca att gtc ctc atg aat tta ctt att ggt ttg gca gtt      3058
Ile Phe Val Pro Ile Val Leu Met Asn Leu Leu Ile Gly Leu Ala Val
                950                 955                 960 ggc gac att gct gag gtc cag aaa cat gca tca ttg aag agg ata gct      3106
Gly Asp Ile Ala Glu Val Gln Lys His Ala Ser Leu Lys Arg Ile Ala
        965                 970                 975
```

| | | |
|---|---|---|
| atg cag gtg gaa ctt cat acc agc tta gag aag aag ctg cca ctt tgg<br>Met Gln Val Glu Leu His Thr Ser Leu Glu Lys Lys Leu Pro Leu Trp<br>    980                   985                   990 | 3154 |
| ttt cta cgc aaa gtg gat cag aaa tcc acc atc gtg tat ccc aac aaa<br>Phe Leu Arg Lys Val Asp Gln Lys Ser Thr Ile Val Tyr Pro Asn Lys<br>    995                  1000               1005 | 3202 |
| ccc aga tct ggt ggg atg tta ttc cat ata ttc tgt ttt tta ttt<br>Pro Arg Ser Gly Gly Met Leu Phe His Ile Phe Cys Phe Leu Phe<br>1010                   1015               1020 | 3247 |
| tgc act ggg gaa ata aga caa gaa ata cca aat gct gat aaa tct<br>Cys Thr Gly Glu Ile Arg Gln Glu Ile Pro Asn Ala Asp Lys Ser<br>1025                   1030               1035 | 3292 |
| tta gaa atg gaa ata tta aag cag aaa tac cgg ctg aag gat ctt<br>Leu Glu Met Glu Ile Leu Lys Gln Lys Tyr Arg Leu Lys Asp Leu<br>1040                   1045               1050 | 3337 |
| act ttt ctc ctg gaa aaa cag cat gag ctc att aaa ctg atc att<br>Thr Phe Leu Leu Glu Lys Gln His Glu Leu Ile Lys Leu Ile Ile<br>1055                   1060               1065 | 3382 |
| cag aag atg gag atc atc tct gag aca gag gat gat gat agc cat<br>Gln Lys Met Glu Ile Ile Ser Glu Thr Glu Asp Asp Asp Ser His<br>1070                   1075               1080 | 3427 |
| tgt tct ttt caa gac agg ttt aag aaa gag cag atg gaa caa agg<br>Cys Ser Phe Gln Asp Arg Phe Lys Lys Glu Gln Met Glu Gln Arg<br>1085                   1090               1095 | 3472 |
| aat agc aga tgg aat act gtg ttg aga gca gtc aag gca aaa aca<br>Asn Ser Arg Trp Asn Thr Val Leu Arg Ala Val Lys Ala Lys Thr<br>1100                   1105               1110 | 3517 |
| cac cat ctt gag cct tag ctcctcagac cttcagtgag gcttctaatg<br>His His Leu Glu Pro<br>1115 | 3565 |
| gggggtgcat gacttgctgg ttctaacttt caatttaaaa agagtgagga agaagcagaa | 3625 |
| tgattcattt tgctgcgtgt gaaatcatgg ttcctgcatg ctgtataaaa gtaaaccatc | 3685 |
| ttttatcctc tattcatatt ttctaccaat cactatgtat tggggatatc tttgcagata | 3745 |
| tgttcaaatt ggactggact ttgatgagat ataatctcat tatttgaatg ggtagaaaat | 3805 |
| gaatttgcta gaacacacat ttttaatgaa agaagtaat aaatgtaact attaagctaa | 3865 |
| aatgcaaatg tcagtactga attcctgctt gttaattaca taatatgtga tgctctagaa | 3925 |
| aatagtcaca agtattaata atgccttaga tgatagtctt aaatattagg ttgaggtcta | 3985 |
| cctaacctaa gctgcttcct ggaaagcttc atgttgaaag aacctatggg tggcaccatg | 4045 |
| tggactttc tgtccctact gtgatgaata gccccaccct tcttgctgtc cccaacacac | 4105 |
| ctgatgtcac tttgagccat atagttgaag tacaaattaa taggccttat gatatgcacg | 4165 |
| aattttacta tagataatat atgttgtttc tggttttgtt tgccaatgag cataataaat | 4225 |
| gtaaaaccta tatagtatcc ctgtgattat tgtatgagcc tttgtttgag atttgaaaac | 4285 |
| aacatggctc catcacatat tccctttttt cttttgatgt ctactcaaat catgaattaa | 4345 |
| tcacatacct catcattaat cttttcaagg tccttctatt gttttgtctg attttctcca | 4405 |
| tcatcctgat tagcatgttt attccctcac taccccagg agatattcac tgtaatgaat | 4465 |
| atgtctttgg ctatgtatgt gtccttgtgt tatgttgtac agtgttgttt tgagtctgtt | 4525 |
| attatttaca cagatgttat tatgctatag cttctatttc tgttttgct tcttattct | 4585 |
| cttataattc tcacttattt cctatttttt ctactcattt ctatttgtta ctcctttta | 4645 |
| ctggacatga tgtttacaag atacaactgt gttactgtat tccatctagt acggggcctt | 4705 |

-continued

```
tggtgtggct tactatttca ttgtgtgcac ccacccaccc accacactgg acttttctag    4765
agatggacag cttggttacc tccaccttcc tgcactcatt ctcaaacata ctgatgttca    4825
tacaaaccag cagagtgctg agggacgata tgtactatta caaaaccaga cacttttaca    4885
ttcatggtcc aacagatcac atggcctaga ggcaatgttg catatacctt aatctttgat    4945
atgaataata tctttgttct ttatatttct taaaacagaa agggtggaaa atcactatac    5005
agaagcaata tccaaagatc tcctgatcat aaagacaagg ggtcttttca gtcttccctc    5065
tcctcaaacc ttgtgtagca ttgcacaata tagatctcag tcaacattca ctgagtgcca    5125
agaatgtgag aaacactgta ccatgcctgt catgcgaaat atttaaataa acagattgtc    5185
ttaca                                                                5190
```

<210> SEQ ID NO 2
<211> LENGTH: 1119
<212> TYPE: PRT
<213> ORGANISM: Homo sapiens

<400> SEQUENCE: 2

```
Met Lys Arg Ser Leu Arg Lys Met Trp Arg Pro Gly Glu Lys Lys Glu
1               5                   10                  15

Pro Gln Gly Val Val Tyr Glu Asp Val Pro Asp Thr Glu Asp Phe
            20                  25                  30

Lys Glu Ser Leu Lys Val Val Phe Glu Gly Ser Ala Tyr Gly Leu Gln
        35                  40                  45

Asn Phe Asn Lys Gln Lys Lys Leu Lys Arg Cys Asp Asp Met Asp Thr
    50                  55                  60

Phe Phe Leu His Tyr Ala Ala Ala Glu Gly Gln Ile Glu Leu Met Glu
65                  70                  75                  80

Lys Ile Thr Arg Asp Ser Ser Leu Glu Val Leu His Glu Met Asp Asp
                85                  90                  95

Tyr Gly Asn Thr Pro Leu His Cys Ala Val Glu Lys Asn Gln Ile Glu
            100                 105                 110

Ser Val Lys Phe Leu Leu Ser Arg Gly Ala Asn Pro Asn Leu Arg Asn
        115                 120                 125

Phe Asn Met Met Ala Pro Leu His Ile Ala Val Gln Gly Met Asn Asn
    130                 135                 140

Glu Val Met Lys Val Leu Leu Glu His Arg Thr Ile Asp Val Asn Leu
145                 150                 155                 160

Glu Gly Glu Asn Gly Asn Thr Ala Val Ile Ile Ala Cys Thr Thr Asn
                165                 170                 175

Asn Ser Glu Ala Leu Gln Ile Leu Leu Lys Lys Gly Ala Lys Pro Cys
            180                 185                 190

Lys Ser Asn Lys Trp Gly Cys Phe Pro Ile His Gln Ala Ala Phe Ser
        195                 200                 205

Gly Ser Lys Glu Cys Met Glu Ile Ile Leu Arg Phe Gly Glu Glu His
    210                 215                 220

Gly Tyr Ser Arg Gln Leu His Ile Asn Phe Met Asn Asn Gly Lys Ala
225                 230                 235                 240

Thr Pro Leu His Leu Ala Val Gln Asn Gly Asp Leu Glu Met Ile Lys
                245                 250                 255

Met Cys Leu Asp Asn Gly Ala Gln Ile Asp Pro Val Glu Lys Gly Arg
            260                 265                 270

Cys Thr Ala Ile His Phe Ala Ala Thr Gln Gly Ala Thr Glu Ile Val
        275                 280                 285
```

```
Lys Leu Met Ile Ser Ser Tyr Ser Gly Ser Val Asp Ile Val Asn Thr
    290                 295                 300

Thr Asp Gly Cys His Glu Thr Met Leu His Arg Ala Ser Leu Phe Asp
305                 310                 315                 320

His His Glu Leu Ala Asp Tyr Leu Ile Ser Val Gly Ala Asp Ile Asn
                    325                 330                 335

Lys Ile Asp Ser Glu Gly Arg Ser Pro Leu Ile Leu Ala Thr Ala Ser
                340                 345                 350

Ala Ser Trp Asn Ile Val Asn Leu Leu Leu Ser Lys Gly Ala Gln Val
            355                 360                 365

Asp Ile Lys Asp Asn Phe Gly Arg Asn Phe Leu His Leu Thr Val Gln
    370                 375                 380

Gln Pro Tyr Gly Leu Lys Asn Leu Arg Pro Glu Phe Met Gln Met Gln
385                 390                 395                 400

Gln Ile Lys Glu Leu Val Met Asp Glu Asp Asn Asp Gly Cys Thr Pro
                405                 410                 415

Leu His Tyr Ala Cys Arg Gln Gly Gly Pro Gly Ser Val Asn Asn Leu
                420                 425                 430

Leu Gly Phe Asn Val Ser Ile His Ser Lys Ser Lys Asp Lys Lys Ser
            435                 440                 445

Pro Leu His Phe Ala Ala Ser Tyr Gly Arg Ile Asn Thr Cys Gln Arg
    450                 455                 460

Leu Leu Gln Asp Ile Ser Asp Thr Arg Leu Leu Asn Glu Gly Asp Leu
465                 470                 475                 480

His Gly Met Thr Pro Leu His Leu Ala Ala Lys Asn Gly His Asp Lys
                485                 490                 495

Val Val Gln Leu Leu Leu Lys Lys Gly Ala Leu Phe Leu Ser Asp His
                500                 505                 510

Asn Gly Trp Thr Ala Leu His His Ala Ser Met Gly Gly Tyr Thr Gln
            515                 520                 525

Thr Met Lys Val Ile Leu Asp Thr Asn Leu Lys Cys Thr Asp Arg Leu
    530                 535                 540

Asp Glu Asp Gly Asn Thr Ala Leu His Phe Ala Ala Arg Glu Gly His
545                 550                 555                 560

Ala Lys Ala Val Ala Leu Leu Leu Ser His Asn Ala Asp Ile Val Leu
                565                 570                 575

Asn Lys Gln Gln Ala Ser Phe Leu His Leu Ala Leu His Asn Lys Arg
                580                 585                 590

Lys Glu Val Val Leu Thr Ile Ile Arg Ser Lys Arg Trp Asp Glu Cys
            595                 600                 605

Leu Lys Ile Phe Ser His Asn Ser Pro Gly Asn Lys Cys Pro Ile Thr
    610                 615                 620

Glu Met Ile Glu Tyr Leu Pro Glu Cys Met Lys Val Leu Leu Asp Phe
625                 630                 635                 640

Cys Met Leu His Ser Thr Glu Asp Lys Ser Cys Arg Asp Tyr Tyr Ile
                645                 650                 655

Glu Tyr Asn Phe Lys Tyr Leu Gln Cys Pro Leu Glu Phe Thr Lys Lys
                660                 665                 670

Thr Pro Thr Gln Asp Val Ile Tyr Glu Pro Leu Thr Ala Leu Asn Ala
            675                 680                 685

Met Val Gln Asn Asn Arg Ile Glu Leu Leu Asn His Pro Val Cys Lys
    690                 695                 700
```

-continued

```
Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
                725                 730                 735

Val Val Asn Ile Lys Pro Gly Met Ala Phe Asn Ser Thr Gly Ile Ile
            740                 745                 750

Asn Glu Thr Ser Asp His Ser Glu Ile Leu Asp Thr Thr Asn Ser Tyr
        755                 760                 765

Leu Ile Lys Thr Cys Met Ile Leu Val Phe Leu Ser Ser Ile Phe Gly
    770                 775                 780

Tyr Cys Lys Glu Ala Gly Gln Ile Phe Gln Gln Lys Arg Asn Tyr Phe
785                 790                 795                 800

Met Asp Ile Ser Asn Val Leu Glu Trp Ile Ile Tyr Thr Thr Gly Ile
                805                 810                 815

Ile Phe Val Leu Pro Leu Phe Val Glu Ile Pro Ala His Leu Gln Trp
            820                 825                 830

Gln Cys Gly Ala Ile Ala Val Tyr Phe Tyr Trp Met Asn Phe Leu Leu
        835                 840                 845

Tyr Leu Gln Arg Phe Glu Asn Cys Gly Ile Phe Ile Val Met Leu Glu
    850                 855                 860

Val Ile Leu Lys Thr Leu Leu Arg Ser Thr Val Val Phe Ile Phe Leu
865                 870                 875                 880

Leu Leu Ala Phe Gly Leu Ser Phe Tyr Ile Leu Leu Asn Leu Gln Asp
                885                 890                 895

Pro Phe Ser Ser Pro Leu Leu Ser Ile Ile Gln Thr Phe Ser Met Met
            900                 905                 910

Leu Gly Asp Ile Asn Tyr Arg Glu Ser Phe Leu Glu Pro Tyr Leu Arg
        915                 920                 925

Asn Glu Leu Ala His Pro Val Leu Ser Phe Ala Gln Leu Val Ser Phe
    930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
                965                 970                 975

Ala Met Gln Val Glu Leu His Thr Ser Leu Glu Lys Lys Leu Pro Leu
            980                 985                 990

Trp Phe Leu Arg Lys Val Asp Gln Lys Ser Thr Ile Val  Tyr Pro Asn
        995                 1000                1005

Lys Pro Arg Ser Gly Gly Met  Leu Phe His Ile Phe  Cys Phe Leu
    1010                1015                1020

Phe Cys  Thr Gly Glu Ile Arg  Gln Glu Ile Pro Asn  Ala Asp Lys
    1025                1030                1035

Ser Leu  Glu Met Glu Ile Leu  Lys Gln Lys Tyr Arg  Leu Lys Asp
    1040                1045                1050

Leu Thr  Phe Leu Leu Glu Lys  Gln His Glu Leu Ile  Lys Leu Ile
    1055                1060                1065

Ile Gln  Lys Met Glu Ile Ile  Ser Glu Thr Glu Asp  Asp Asp Ser
    1070                1075                1080

His Cys  Ser Phe Gln Asp Arg  Phe Lys Lys Glu Gln  Met Glu Gln
    1085                1090                1095

Arg Asn  Ser Arg Trp Asn Thr  Val Leu Arg Ala Val  Lys Ala Lys
    1100                1105                1110

Thr His  His Leu Glu Pro
```

-continued

```
                1115

<210> SEQ ID NO 3
<211> LENGTH: 5621
<212> TYPE: DNA
<213> ORGANISM: Homo sapiens
<220> FEATURE:
<221> NAME/KEY: CDS
<222> LOCATION: (41)..(3355)

<400> SEQUENCE: 3
aagaaaatcc tgcttgacaa aaaccgtcac ttaggaaaag atg tcc ttt cgg gca       55
                                             Met Ser Phe Arg Ala
                                             1               5 gcc agg ctc agc atg agg aac aga agg aat gac act ctg gac agc acc      103
Ala Arg Leu Ser Met Arg Asn Arg Arg Asn Asp Thr Leu Asp Ser Thr
             10                  15                  20 cgg acc ctg tac tcc agc gcg tct cgg agc aca gac ttg tct tac agt      151
Arg Thr Leu Tyr Ser Ser Ala Ser Arg Ser Thr Asp Leu Ser Tyr Ser
         25                  30                  35 gaa agc gac ttg gtg aat ttt att caa gca aat ttt aag aaa cga gaa      199
Glu Ser Asp Leu Val Asn Phe Ile Gln Ala Asn Phe Lys Lys Arg Glu
     40                  45                  50 tgt gtc ttc ttt acc aaa gat tcc aag gcc acg gag aat gtg tgc aag      247
Cys Val Phe Phe Thr Lys Asp Ser Lys Ala Thr Glu Asn Val Cys Lys
 55                  60                  65 tgt ggc tat gcc cag agc cag cac atg gaa ggc acc cag atc aac caa      295
Cys Gly Tyr Ala Gln Ser Gln His Met Glu Gly Thr Gln Ile Asn Gln
 70                  75                  80                  85 agt gag aaa tgg aac tac aag aaa cac acc aag gaa ttt cct acc gac      343
Ser Glu Lys Trp Asn Tyr Lys Lys His Thr Lys Glu Phe Pro Thr Asp
             90                  95                 100 gcc ttt ggg gat att cag ttt gag aca ctg ggg aag aaa ggg aag tat      391
Ala Phe Gly Asp Ile Gln Phe Glu Thr Leu Gly Lys Lys Gly Lys Tyr
        105                 110                 115 ata cgt ctg tcc tgc gac acg gac gcg gaa atc ctt tac gag ctg ctg      439
Ile Arg Leu Ser Cys Asp Thr Asp Ala Glu Ile Leu Tyr Glu Leu Leu
    120                 125                 130 acc cag cac tgg cac ctg aaa aca ccc aac ctg gtc att tct gtg acc      487
Thr Gln His Trp His Leu Lys Thr Pro Asn Leu Val Ile Ser Val Thr
135                 140                 145 ggg ggc gcc aag aac ttc gcc ctg aag ccg cgc atg cgc aag atc ttc      535
Gly Gly Ala Lys Asn Phe Ala Leu Lys Pro Arg Met Arg Lys Ile Phe
150                 155                 160                 165 agc cgg ctc atc tac atc gcg cag tcc aaa ggt gct tgg att ctc acg      583
Ser Arg Leu Ile Tyr Ile Ala Gln Ser Lys Gly Ala Trp Ile Leu Thr
            170                 175                 180 gga ggc acc cat tat ggc ctg atg aag tac atc ggg gag gtg gtg aga      631
Gly Gly Thr His Tyr Gly Leu Met Lys Tyr Ile Gly Glu Val Val Arg
        185                 190                 195 gat aac acc atc agc agg agt tca gag gag aat att gtg gcc att ggc      679
Asp Asn Thr Ile Ser Arg Ser Ser Glu Glu Asn Ile Val Ala Ile Gly
    200                 205                 210 ata gca gct tgg ggc atg gtc tcc aac cgg gac acc ctc atc agg aat      727
Ile Ala Ala Trp Gly Met Val Ser Asn Arg Asp Thr Leu Ile Arg Asn
215                 220                 225 tgc gat gct gag ggc tat ttt tta gcc cag tac ctt atg gat gac ttc      775
Cys Asp Ala Glu Gly Tyr Phe Leu Ala Gln Tyr Leu Met Asp Asp Phe
230                 235                 240                 245 aca aga gat cca ctg tat atc ctg gac aac aac cac aca cat ttg ctg      823
Thr Arg Asp Pro Leu Tyr Ile Leu Asp Asn Asn His Thr His Leu Leu
```

-continued

|     |     |     |     |     |     |     |     |     |     |     |     |     |     |     |     |     |
|---|---|---|---|---|---|---|---|---|---|---|---|---|---|---|---|---|
|     |     |     | 250 |     |     |     | 255 |     |     |     | 260 |     |     |     |     |     |
| ctc | gtg | gac | aat | ggc | tgt | cat | gga | cat | ccc | act | gtc | gaa | gca | aag | ctc | 871 |
| Leu | Val | Asp | Asn | Gly | Cys | His | Gly | His | Pro | Thr | Val | Glu | Ala | Lys | Leu |     |
|     |     |     | 265 |     |     |     | 270 |     |     |     | 275 |     |     |     |     |     |
| cgg | aat | cag | cta | gag | aag | tat | atc | tct | gag | cgc | act | att | caa | gat | tcc | 919 |
| Arg | Asn | Gln | Leu | Glu | Lys | Tyr | Ile | Ser | Glu | Arg | Thr | Ile | Gln | Asp | Ser |     |
|     |     | 280 |     |     |     |     | 285 |     |     |     |     | 290 |     |     |     |     |
| aac | tat | ggt | ggc | aag | atc | ccc | att | gtg | tgt | ttt | gcc | caa | gga | ggt | gga | 967 |
| Asn | Tyr | Gly | Gly | Lys | Ile | Pro | Ile | Val | Cys | Phe | Ala | Gln | Gly | Gly | Gly |     |
|     | 295 |     |     |     |     | 300 |     |     |     |     | 305 |     |     |     |     |     |
| aaa | gag | act | ttg | aaa | gcc | atc | aat | acc | tcc | atc | aaa | aat | aaa | att | cct | 1015 |
| Lys | Glu | Thr | Leu | Lys | Ala | Ile | Asn | Thr | Ser | Ile | Lys | Asn | Lys | Ile | Pro |     |
| 310 |     |     |     |     | 315 |     |     |     |     | 320 |     |     |     |     | 325 |     |
| tgt | gtg | gtg | gtg | gaa | ggc | tcg | ggc | cag | atc | gct | gat | gtg | atc | gct | agc | 1063 |
| Cys | Val | Val | Val | Glu | Gly | Ser | Gly | Gln | Ile | Ala | Asp | Val | Ile | Ala | Ser |     |
|     |     |     |     | 330 |     |     |     |     | 335 |     |     |     |     | 340 |     |     |
| ctg | gtg | gag | gtg | gag | gat | gcc | ctg | aca | tct | tct | gcc | gtc | aag | gag | aag | 1111 |
| Leu | Val | Glu | Val | Glu | Asp | Ala | Leu | Thr | Ser | Ser | Ala | Val | Lys | Glu | Lys |     |
|     |     |     | 345 |     |     |     |     | 350 |     |     |     |     | 355 |     |     |     |
| ctg | gtg | cgc | ttt | tta | ccc | cgc | acg | gtg | tcc | cgg | ctg | cct | gag | gag | gag | 1159 |
| Leu | Val | Arg | Phe | Leu | Pro | Arg | Thr | Val | Ser | Arg | Leu | Pro | Glu | Glu | Glu |     |
|     |     | 360 |     |     |     |     | 365 |     |     |     |     | 370 |     |     |     |     |
| act | gag | agt | tgg | atc | aaa | tgg | ctc | aaa | gaa | att | ctc | gaa | tgt | tct | cac | 1207 |
| Thr | Glu | Ser | Trp | Ile | Lys | Trp | Leu | Lys | Glu | Ile | Leu | Glu | Cys | Ser | His |     |
|     | 375 |     |     |     |     | 380 |     |     |     |     | 385 |     |     |     |     |     |
| cta | tta | aca | gtt | att | aaa | atg | gaa | gaa | gct | ggg | gat | gaa | att | gtg | agc | 1255 |
| Leu | Leu | Thr | Val | Ile | Lys | Met | Glu | Glu | Ala | Gly | Asp | Glu | Ile | Val | Ser |     |
| 390 |     |     |     |     | 395 |     |     |     |     | 400 |     |     |     |     | 405 |     |
| aat | gcc | atc | tcc | tac | gct | cta | tac | aaa | gcc | ttc | agc | acc | agt | gag | caa | 1303 |
| Asn | Ala | Ile | Ser | Tyr | Ala | Leu | Tyr | Lys | Ala | Phe | Ser | Thr | Ser | Glu | Gln |     |
|     |     |     |     | 410 |     |     |     |     | 415 |     |     |     |     | 420 |     |     |
| gac | aag | gat | aac | tgg | aat | ggg | cag | ctg | aag | ctt | ctg | ctg | gag | tgg | aac | 1351 |
| Asp | Lys | Asp | Asn | Trp | Asn | Gly | Gln | Leu | Lys | Leu | Leu | Leu | Glu | Trp | Asn |     |
|     |     |     | 425 |     |     |     |     | 430 |     |     |     |     | 435 |     |     |     |
| cag | ctg | gac | tta | gcc | aat | gat | gag | att | ttc | acc | aat | gac | cgc | cga | tgg | 1399 |
| Gln | Leu | Asp | Leu | Ala | Asn | Asp | Glu | Ile | Phe | Thr | Asn | Asp | Arg | Arg | Trp |     |
|     |     | 440 |     |     |     |     | 445 |     |     |     |     | 450 |     |     |     |     |
| gag | tct | gct | gac | ctt | caa | gaa | gtc | atg | ttt | acg | gct | ctc | ata | aag | gac | 1447 |
| Glu | Ser | Ala | Asp | Leu | Gln | Glu | Val | Met | Phe | Thr | Ala | Leu | Ile | Lys | Asp |     |
|     | 455 |     |     |     |     | 460 |     |     |     |     | 465 |     |     |     |     |     |
| aga | ccc | aag | ttt | gtc | cgc | ctc | ttt | ctg | gag | aat | ggc | ttg | aac | cta | cgg | 1495 |
| Arg | Pro | Lys | Phe | Val | Arg | Leu | Phe | Leu | Glu | Asn | Gly | Leu | Asn | Leu | Arg |     |
| 470 |     |     |     |     | 475 |     |     |     |     | 480 |     |     |     |     | 485 |     |
| aag | ttt | ctc | acc | cat | gat | gtc | ctc | act | gaa | ctc | ttc | tcc | aac | cac | ttc | 1543 |
| Lys | Phe | Leu | Thr | His | Asp | Val | Leu | Thr | Glu | Leu | Phe | Ser | Asn | His | Phe |     |
|     |     |     |     | 490 |     |     |     |     | 495 |     |     |     |     | 500 |     |     |
| agc | acg | ctt | gtg | tac | cgg | aat | ctg | cag | atc | gcc | aag | aat | tcc | tat | aat | 1591 |
| Ser | Thr | Leu | Val | Tyr | Arg | Asn | Leu | Gln | Ile | Ala | Lys | Asn | Ser | Tyr | Asn |     |
|     |     |     | 505 |     |     |     |     | 510 |     |     |     |     | 515 |     |     |     |
| gat | gcc | ctc | ctc | acg | ttt | gtc | tgg | aaa | ctg | gtt | gcg | aac | ttc | cga | aga | 1639 |
| Asp | Ala | Leu | Leu | Thr | Phe | Val | Trp | Lys | Leu | Val | Ala | Asn | Phe | Arg | Arg |     |
|     |     | 520 |     |     |     |     | 525 |     |     |     |     | 530 |     |     |     |     |
| ggc | ttc | cgg | aag | gaa | gac | aga | aat | ggc | cgg | gac | gag | atg | gac | ata | gaa | 1687 |
| Gly | Phe | Arg | Lys | Glu | Asp | Arg | Asn | Gly | Arg | Asp | Glu | Met | Asp | Ile | Glu |     |
|     | 535 |     |     |     |     | 540 |     |     |     |     | 545 |     |     |     |     |     |
| ctc | cac | gac | gtg | tct | cct | att | act | cgg | cac | ccc | ctg | caa | gct | ctc | ttc | 1735 |
| Leu | His | Asp | Val | Ser | Pro | Ile | Thr | Arg | His | Pro | Leu | Gln | Ala | Leu | Phe |     |
| 550 |     |     |     |     | 555 |     |     |     |     | 560 |     |     |     |     | 565 |     |
| atc | tgg | gcc | att | ctt | cag | aat | aag | aag | gaa | ctc | tcc | aaa | gtc | att | tgg | 1783 |

|      |      |      |      |      |      |      |      |      |      |      |      |      |      |
|------|------|------|------|------|------|------|------|------|------|------|------|------|------|
| Ile  | Trp  | Ala  | Ile  | Leu  | Gln  | Asn  | Lys  | Lys  | Glu  | Leu  | Ser  | Lys  | Val  | Ile  | Trp  |
|      |      |      |      | 570  |      |      |      | 575  |      |      |      | 580  |

```
gag cag acc agg ggc tgc act ctg gca gcc ctg gga gcc agc aag ctt     1831
Glu Gln Thr Arg Gly Cys Thr Leu Ala Ala Leu Gly Ala Ser Lys Leu
            585                 590                 595 ctg aag act ctg gcc aaa gtg aag aac gac atc aat gct gct ggg gag     1879
Leu Lys Thr Leu Ala Lys Val Lys Asn Asp Ile Asn Ala Ala Gly Glu
            600                 605                 610 tcc gag gag ctg gct aat gag tac gag acc cgg gct gtt gag ctg ttc     1927
Ser Glu Glu Leu Ala Asn Glu Tyr Glu Thr Arg Ala Val Glu Leu Phe
    615                 620                 625 act gag tgt tac agc agc gat gaa gac ttg gca gaa cag ctg ctg gtc     1975
Thr Glu Cys Tyr Ser Ser Asp Glu Asp Leu Ala Glu Gln Leu Leu Val
630                 635                 640                 645 tat tcc tgt gaa gct tgg ggt gga agc aac tgt ctg gag ctg gcg gtg     2023
Tyr Ser Cys Glu Ala Trp Gly Gly Ser Asn Cys Leu Glu Leu Ala Val
                650                 655                 660 gag gcc aca gac cag cat ttc atc gcc cag cct ggg gtc cag aat ttt     2071
Glu Ala Thr Asp Gln His Phe Ile Ala Gln Pro Gly Val Gln Asn Phe
            665                 670                 675 ctt tct aag caa tgg tat gga gag att tcc cga gac acc aag aac tgg     2119
Leu Ser Lys Gln Trp Tyr Gly Glu Ile Ser Arg Asp Thr Lys Asn Trp
            680                 685                 690 aag att atc ctg tgt ctg ttt att ata ccc ttg gtg ggc tgt ggc ttt     2167
Lys Ile Ile Leu Cys Leu Phe Ile Ile Pro Leu Val Gly Cys Gly Phe
            695                 700                 705 gta tca ttt agg aag aaa cct gtc gac aag cac aag aag ctg ctt tgg     2215
Val Ser Phe Arg Lys Lys Pro Val Asp Lys His Lys Lys Leu Leu Trp
710                 715                 720                 725 tac tat gtg gcg ttc ttc acc tcc ccc ttc gtg gtc ttc tcc tgg aat     2263
Tyr Tyr Val Ala Phe Phe Thr Ser Pro Phe Val Val Phe Ser Trp Asn
                730                 735                 740 gtg gtc ttc tac atc gcc ttc ctc ctg ctg ttt gcc tac gtg ctg ctc     2311
Val Val Phe Tyr Ile Ala Phe Leu Leu Leu Phe Ala Tyr Val Leu Leu
            745                 750                 755 atg gat ttc cat tcg gtg cca cac ccc ccc gag ctg gtc ctg tac tcg     2359
Met Asp Phe His Ser Val Pro His Pro Pro Glu Leu Val Leu Tyr Ser
            760                 765                 770 ctg gtc ttt gtc ctc ttc tgt gat gaa gtg aga cag tgg tac gta aat     2407
Leu Val Phe Val Leu Phe Cys Asp Glu Val Arg Gln Trp Tyr Val Asn
775                 780                 785 ggg gtg aat tat ttt act gac ctg tgg aat gtg atg gac acg ctg ggg     2455
Gly Val Asn Tyr Phe Thr Asp Leu Trp Asn Val Met Asp Thr Leu Gly
790                 795                 800                 805 ctt ttt tac ttc ata gca gga att gta ttt cgg ctc cac tct tct aat     2503
Leu Phe Tyr Phe Ile Ala Gly Ile Val Phe Arg Leu His Ser Ser Asn
                810                 815                 820 aaa agc tct ttg tat tct gga cga gtc att ttc tgt ctg gac tac att     2551
Lys Ser Ser Leu Tyr Ser Gly Arg Val Ile Phe Cys Leu Asp Tyr Ile
            825                 830                 835 att ttc act cta aga ttg atc cac att ttt act gta agc aga aac tta     2599
Ile Phe Thr Leu Arg Leu Ile His Ile Phe Thr Val Ser Arg Asn Leu
            840                 845                 850 gga ccc aag att ata atg ctg cag agg atg ctg atc gat gtg ttc ttc     2647
Gly Pro Lys Ile Ile Met Leu Gln Arg Met Leu Ile Asp Val Phe Phe
855                 860                 865 ttc ctg ttc ctc ttt gcg gtg tgg atg gtg gcc ttt ggc gtg gcc agg     2695
Phe Leu Phe Leu Phe Ala Val Trp Met Val Ala Phe Gly Val Ala Arg
870                 875                 880                 885
```

|  |  |
|---|---|
| caa ggg atc ctt agg cag aat gag cag cgc tgg agg tgg ata ttc cgt<br>Gln Gly Ile Leu Arg Gln Asn Glu Gln Arg Trp Arg Trp Ile Phe Arg<br>            890                 895                 900 | 2743 |
| tcg gtc atc tac gag ccc tac ctg gcc atg ttc ggc cag gtg ccc agt<br>Ser Val Ile Tyr Glu Pro Tyr Leu Ala Met Phe Gly Gln Val Pro Ser<br>        905                 910                 915 | 2791 |
| gac gtg gat ggt acc acg tat gac ttt gcc cac tgc acc ttc act ggg<br>Asp Val Asp Gly Thr Thr Tyr Asp Phe Ala His Cys Thr Phe Thr Gly<br>    920                 925                 930 | 2839 |
| aat gag tcc aag cca ctg tgt gtg gag ctg gat gag cac aac ctg ccc<br>Asn Glu Ser Lys Pro Leu Cys Val Glu Leu Asp Glu His Asn Leu Pro<br>935                 940                 945 | 2887 |
| cgg ttc ccc gag tgg atc acc atc ccc ctg gtg tgc atc tac atg tta<br>Arg Phe Pro Glu Trp Ile Thr Ile Pro Leu Val Cys Ile Tyr Met Leu<br>950                 955                 960                 965 | 2935 |
| tcc acc aac atc ctg ctg gtc aac ctg ctg gtc gcc atg ttt ggc tac<br>Ser Thr Asn Ile Leu Leu Val Asn Leu Leu Val Ala Met Phe Gly Tyr<br>            970                 975                 980 | 2983 |
| acg gtg ggc acc gtc cag gag aac aat gac cag gtc tgg aag ttc cag<br>Thr Val Gly Thr Val Gln Glu Asn Asn Asp Gln Val Trp Lys Phe Gln<br>        985                 990                 995 | 3031 |
| agg tac ttc ctg gtg cag gag tac tgc agc cgc ctc aat atc ccc<br>Arg Tyr Phe Leu Val Gln Glu Tyr Cys Ser Arg Leu Asn Ile Pro<br>    1000                1005                1010 | 3076 |
| ttc ccc ttc atc gtc ttc gct tac ttc tac atg gtg gtg aag aag<br>Phe Pro Phe Ile Val Phe Ala Tyr Phe Tyr Met Val Val Lys Lys<br>    1015                1020                1025 | 3121 |
| tgc ttc aag tgt tgc tgc aag gag aaa aac atg gag tct tct gtc<br>Cys Phe Lys Cys Cys Cys Lys Glu Lys Asn Met Glu Ser Ser Val<br>    1030                1035                1040 | 3166 |
| tgc tgt ttc aaa aat gaa gac aat gag act ctg gca tgg gag ggt<br>Cys Cys Phe Lys Asn Glu Asp Asn Glu Thr Leu Ala Trp Glu Gly<br>    1045                1050                1055 | 3211 |
| gtc atg aag gaa aac tac ctt gtc aag atc aac aca aaa gcc aac<br>Val Met Lys Glu Asn Tyr Leu Val Lys Ile Asn Thr Lys Ala Asn<br>    1060                1065                1070 | 3256 |
| gac acc tca gag gaa atg agg cat cga ttt aga caa ctg gat aca<br>Asp Thr Ser Glu Glu Met Arg His Arg Phe Arg Gln Leu Asp Thr<br>    1075                1080                1085 | 3301 |
| aag ctt aat gat ctc aag ggt ctt ctg aaa gag att gct aat aaa<br>Lys Leu Asn Asp Leu Lys Gly Leu Leu Lys Glu Ile Ala Asn Lys<br>    1090                1095                1100 | 3346 |
| atc aaa taa aactgtatga actctaatgg agaaaatct aattatagca<br>Ile Lys | 3395 |
| agatcatatt aaggaatgct gatgaacaat tttgctatcg actactaaat gagagatttt | 3455 |
| cagacccctg gtacatggt ggatgatttt aaatcaccct agtgtgctga gaccttgaga | 3515 |
| ataaagtgtg tgattggttt catacttgaa gacggatata aaggaagaat atttcctta | 3575 |
| tgtgtttctc cagaatggtg cctgtttctc tctgtgtctc aatgcctggg actggaggtt | 3635 |
| gatagtttaa gtgtgttctt accgcctcct ttttccttta atcttatttt tgatgaacac | 3695 |
| atatatagga gaacatctat cctatgaata agaacctggt catgctttac tcctgtattg | 3755 |
| ttattttgtt catttccaat tgattctcta cttttccctt ttttgtatta tgtgactaat | 3815 |
| tagttggcat attgttaaaa gtctctcaaa ttaggccaga ttctaaaaca tgctgcagca | 3875 |
| agaggacccc gctctcttca ggaaaagtgt tttcatttct caggatgctt cttacctgtc | 3935 |
| agaggaggtg acaaggcagt ctcttgctct cttggactca ccaggctcct attgaaggaa | 3995 |

```
ccaccccccat tcctaaatat gtgaaaagtc gcccaaaatg caaccttgaa aggcactact    4055
gactttgttc ttattggata ctcctcttat tattttttcca ttaaaaataa tagctggcta    4115
ttatagaaaa tttagaccat acagagatgt agaaagaaca taaattgtcc ccattacctt    4175
aaggtaatca ctgctaacaa tttctggatg gttttttcaag tctatttttt ttctatgtat    4235
gtctcaattc tctttcaaaa ttttacagaa tgttatcata ctacatatat acttttttatg   4295 taagcttttt cacttagtat tttatcaaat atgtttttat tatattcata gccttcttaa    4355
acattatatc aataattgca taataggcaa cctctagcga ttaccataat tttgctcatt    4415
gaaggctatc tccagttgat cattgggatg agcatctttg tgcatgaatc ctattgctgt    4475
atttgggaaa attttccaag gttagattcc aataaatatc tatttattat taaatattaa    4535
aatatctatt tattattaaa accatttata aggcttttttc ataaatgtat agcaaatagg   4595
aattattaac ttgagcataa gatatgagat acatgaacct gaactattaa aataaaatat    4655
tatatttaac ccttagttta agaagaagtc aatatgctta tttaaatatt atggatggtg    4715
ggcagatcac ttgaggtcag gagttcgaga ccagcctggc caacatggca aaaccacatc    4775
tctactaaaa ataaaaaaat tagctgggtg tggtggtgca ctcctgtaat cccagctact    4835
cagaaggctg aggtacaaga attgctgaa cctgggaggc ggaggttgca gtgaaccaag    4895
attgcaccac tgcactccag ccggggtgac agagtgagac tccgactgaa aataaataaa    4955
taaataaata aataaataaa taatatat ggatggtgaa gggaatggta tagaattgga    5015
gagattatct tactgaacac ctgtagtccc agctttctct ggaagtggtc gtatttgagc    5075
aggatgtgca caaggcaatt gaatgcccca taattagttt ctcagctttg aatacactat    5135
aaactcactg gctgaaggag gaaattttag aaggaagcta ctaaaagatc taatttgaaa    5195
aactacaaaa gcattaacta aaaaagttta ttttcctttt gtctgggcag tagtgaaaat    5255
aactactcac aacattcact atgtttgcaa ggaattaaca caaataaaag atgcttttt    5315 acttaaacac caagacagaa aacttgccca atactgagaa gcaacttgca ttagagaggg    5375
aactgttaaa tgttttcaac ccagttcatc tggtggatgt ttttgcaggt tactctgaga    5435
attttgctta tgaaaaatca ttatttttag tgtagttcac aataatgtat tgaacatact    5495
tctaatcaaa ggtgctatgt ccttgtgtat ggtactaaat gtgtcctgtg tacttttgca    5555
caactgagaa tcctgcagct tggtttaatg agtgtgttca tgaaataaat aatggaggaa    5615
ttgtca                                                              5621
```

<210> SEQ ID NO 4
<211> LENGTH: 1104
<212> TYPE: PRT
<213> ORGANISM: Homo sapiens

<400> SEQUENCE: 4

```
Met Ser Phe Arg Ala Ala Arg Leu Ser Met Arg Asn Arg Arg Asn Asp
1               5                   10                  15

Thr Leu Asp Ser Thr Arg Thr Leu Tyr Ser Ser Ala Ser Arg Ser Thr
            20                  25                  30

Asp Leu Ser Tyr Ser Glu Ser Asp Leu Val Asn Phe Ile Gln Ala Asn
        35                  40                  45

Phe Lys Lys Arg Glu Cys Val Phe Phe Thr Lys Asp Ser Lys Ala Thr
    50                  55                  60

Glu Asn Val Cys Lys Cys Gly Tyr Ala Gln Ser Gln His Met Glu Gly
65                  70                  75                  80
```

-continued

```
Thr Gln Ile Asn Gln Ser Glu Lys Trp Asn Tyr Lys Lys His Thr Lys
             85                  90                  95
Glu Phe Pro Thr Asp Ala Phe Gly Asp Ile Gln Phe Glu Thr Leu Gly
            100                 105                 110
Lys Lys Gly Lys Tyr Ile Arg Leu Ser Cys Asp Thr Asp Ala Glu Ile
        115                 120                 125
Leu Tyr Glu Leu Leu Thr Gln His Trp His Leu Lys Thr Pro Asn Leu
    130                 135                 140
Val Ile Ser Val Thr Gly Gly Ala Lys Asn Phe Ala Leu Lys Pro Arg
145                 150                 155                 160
Met Arg Lys Ile Phe Ser Arg Leu Ile Tyr Ile Ala Gln Ser Lys Gly
                165                 170                 175
Ala Trp Ile Leu Thr Gly Gly Thr His Tyr Gly Leu Met Lys Tyr Ile
            180                 185                 190
Gly Glu Val Val Arg Asp Asn Thr Ile Ser Arg Ser Ser Glu Glu Asn
        195                 200                 205
Ile Val Ala Ile Gly Ile Ala Ala Trp Gly Met Val Ser Asn Arg Asp
    210                 215                 220
Thr Leu Ile Arg Asn Cys Asp Ala Glu Gly Tyr Phe Leu Ala Gln Tyr
225                 230                 235                 240
Leu Met Asp Asp Phe Thr Arg Asp Pro Leu Tyr Ile Leu Asp Asn Asn
                245                 250                 255
His Thr His Leu Leu Val Asp Asn Gly Cys His Gly His Pro Thr
            260                 265                 270
Val Glu Ala Lys Leu Arg Asn Gln Leu Glu Lys Tyr Ile Ser Glu Arg
        275                 280                 285
Thr Ile Gln Asp Ser Asn Tyr Gly Gly Lys Ile Pro Ile Val Cys Phe
    290                 295                 300
Ala Gln Gly Gly Gly Lys Glu Thr Leu Lys Ala Ile Asn Thr Ser Ile
305                 310                 315                 320
Lys Asn Lys Ile Pro Cys Val Val Val Glu Gly Ser Gly Gln Ile Ala
                325                 330                 335
Asp Val Ile Ala Ser Leu Val Glu Val Glu Asp Ala Leu Thr Ser Ser
            340                 345                 350
Ala Val Lys Glu Lys Leu Val Arg Phe Leu Pro Arg Thr Val Ser Arg
        355                 360                 365
Leu Pro Glu Glu Glu Thr Glu Ser Trp Ile Lys Trp Leu Lys Glu Ile
    370                 375                 380
Leu Glu Cys Ser His Leu Leu Thr Val Ile Lys Met Glu Glu Ala Gly
385                 390                 395                 400
Asp Glu Ile Val Ser Asn Ala Ile Ser Tyr Ala Leu Tyr Lys Ala Phe
                405                 410                 415
Ser Thr Ser Glu Gln Asp Lys Asp Asn Trp Asn Gly Gln Leu Lys Leu
            420                 425                 430
Leu Leu Glu Trp Asn Gln Leu Asp Leu Ala Asn Asp Glu Ile Phe Thr
        435                 440                 445
Asn Asp Arg Arg Trp Glu Ser Ala Asp Leu Gln Glu Val Met Phe Thr
    450                 455                 460
Ala Leu Ile Lys Asp Arg Pro Lys Phe Val Arg Leu Phe Leu Glu Asn
465                 470                 475                 480
Gly Leu Asn Leu Arg Lys Phe Leu Thr His Asp Val Leu Thr Glu Leu
                485                 490                 495
Phe Ser Asn His Phe Ser Thr Leu Val Tyr Arg Asn Leu Gln Ile Ala
```

-continued

```
                500             505             510
Lys Asn Ser Tyr Asn Asp Ala Leu Leu Thr Phe Val Trp Lys Leu Val
            515                 520                 525

Ala Asn Phe Arg Arg Gly Phe Arg Lys Glu Asp Arg Asn Gly Arg Asp
            530                 535                 540

Glu Met Asp Ile Glu Leu His Asp Val Ser Pro Ile Thr Arg His Pro
545                 550                 555                 560

Leu Gln Ala Leu Phe Ile Trp Ala Ile Leu Gln Asn Lys Lys Glu Leu
                565                 570                 575

Ser Lys Val Ile Trp Glu Gln Thr Arg Gly Cys Thr Leu Ala Ala Leu
            580                 585                 590

Gly Ala Ser Lys Leu Leu Lys Thr Leu Ala Lys Val Lys Asn Asp Ile
            595                 600                 605

Asn Ala Ala Gly Glu Ser Glu Leu Ala Asn Glu Tyr Glu Thr Arg
            610                 615                 620

Ala Val Glu Leu Phe Thr Glu Cys Tyr Ser Ser Asp Glu Asp Leu Ala
625                 630                 635                 640

Glu Gln Leu Leu Val Tyr Ser Cys Glu Ala Trp Gly Gly Ser Asn Cys
                645                 650                 655

Leu Glu Leu Ala Val Glu Ala Thr Asp Gln His Phe Ile Ala Gln Pro
                660                 665                 670

Gly Val Gln Asn Phe Leu Ser Lys Gln Trp Tyr Gly Ile Ser Arg
            675                 680                 685

Asp Thr Lys Asn Trp Lys Ile Ile Leu Cys Leu Phe Ile Ile Pro Leu
            690                 695                 700

Val Gly Cys Gly Phe Val Ser Phe Arg Lys Lys Pro Val Asp Lys His
705                 710                 715                 720

Lys Lys Leu Leu Trp Tyr Tyr Val Ala Phe Phe Thr Ser Pro Phe Val
                725                 730                 735

Val Phe Ser Trp Asn Val Val Phe Tyr Ile Ala Phe Leu Leu Leu Phe
                740                 745                 750

Ala Tyr Val Leu Leu Met Asp Phe His Ser Val Pro His Pro Pro Glu
            755                 760                 765

Leu Val Leu Tyr Ser Leu Val Phe Val Leu Phe Cys Asp Glu Val Arg
            770                 775                 780

Gln Trp Tyr Val Asn Gly Val Asn Tyr Phe Thr Asp Leu Trp Asn Val
785                 790                 795                 800

Met Asp Thr Leu Gly Leu Phe Tyr Phe Ile Ala Gly Ile Val Phe Arg
                805                 810                 815

Leu His Ser Ser Asn Lys Ser Ser Leu Tyr Ser Gly Arg Val Ile Phe
                820                 825                 830

Cys Leu Asp Tyr Ile Ile Phe Thr Leu Arg Leu Ile His Ile Phe Thr
            835                 840                 845

Val Ser Arg Asn Leu Gly Pro Lys Ile Ile Met Leu Gln Arg Met Leu
            850                 855                 860

Ile Asp Val Phe Phe Phe Leu Phe Leu Phe Ala Val Trp Met Val Ala
865                 870                 875                 880

Phe Gly Val Ala Arg Gln Gly Ile Leu Arg Gln Asn Glu Gln Arg Trp
                885                 890                 895

Arg Trp Ile Phe Arg Ser Val Ile Tyr Glu Pro Tyr Leu Ala Met Phe
                900                 905                 910

Gly Gln Val Pro Ser Asp Val Asp Gly Thr Thr Tyr Asp Phe Ala His
            915                 920                 925
```

```
Cys Thr Phe Thr Gly Asn Glu Ser Lys Pro Leu Cys Val Glu Leu Asp
    930             935             940

Glu His Asn Leu Pro Arg Phe Pro Glu Trp Ile Thr Ile Pro Leu Val
945             950             955             960

Cys Ile Tyr Met Leu Ser Thr Asn Ile Leu Val Asn Leu Leu Val
            965             970             975

Ala Met Phe Gly Tyr Thr Val Gly Thr Val Gln Glu Asn Asn Asp Gln
            980             985             990

Val Trp Lys Phe Gln Arg Tyr Phe Leu Val Gln Glu Tyr Cys Ser Arg
        995             1000            1005

Leu Asn Ile Pro Phe Pro Phe Ile Val Phe Ala Tyr Phe Tyr Met
    1010            1015            1020

Val Val Lys Lys Cys Phe Lys Cys Cys Cys Lys Glu Lys Asn Met
    1025            1030            1035

Glu Ser Ser Val Cys Cys Phe Lys Asn Glu Asp Asn Glu Thr Leu
    1040            1045            1050

Ala Trp Glu Gly Val Met Lys Glu Asn Tyr Leu Val Lys Ile Asn
    1055            1060            1065

Thr Lys Ala Asn Asp Thr Ser Glu Glu Met Arg His Arg Phe Arg
    1070            1075            1080

Gln Leu Asp Thr Lys Leu Asn Asp Leu Lys Gly Leu Leu Lys Glu
    1085            1090            1095

Ile Ala Asn Lys Ile Lys
    1100
```

TRPA1 ACTIVITY INHIBITOR

TECHNICAL FIELD

The present invention relates to a TRPA1 activity-inhibitor. More specifically, the present invention relates to a TRPA1 activity-inhibitor, a method for inhibiting TRPA1 activity, an external preparation and an irritative sensation-mitigating agent.

BACKGROUND ART

An external preparation such as an external preparation for skin or an external preparation for scalp hair contains, for example, a refreshing agent, parabens, an alkaline agent, and the like. It has been found by the present inventors that the refreshing agent, the parabens and the alkaline agent activate TRPA1 which is one of transient receptor potential channels, and that the refreshing agent, the parabens and the alkaline agent cause unpleasant irritative sensation via the resulting activated TRPA1 (see, for example, Patent Literatures 1 to 5). However, in recent years, an external preparation which does not cause unpleasant irritative sensation or which has weak unpleasant irritative sensation is preferred, because safety consciousness of a user has been increased.

Additionally, various compounds which inhibit TRPA1 activity have been found by the present inventors (see Patent Literatures 4 and 5). However, these compounds have a characteristic smell. Accordingly, a countermeasure against the smell such as masking of the smell by other components may be desired in some cases, when the external preparation and the like contain these compounds.

PRIOR ART LITERATURES

Patent Literatures

Patent Literature 1: Japanese Patent Laid-Open No. 2008-79528

Patent Literature 2: Japanese Patent Laid-Open No. 2009-82053

Patent Literature 3: Japanese Patent Laid-Open No. 2009-225733

Patent Literature 4: Japanese Patent Laid-Open No. 2012-62304

Patent Literature 5: Japanese Patent Laid-Open No. 2014-65690

SUMMARY OF THE INVENTION

Problems to be Solved by the Invention

The present invention has been accomplished in view of the above-mentioned prior art. An object of the present invention is to provide a TRPA1 activity-inhibitor and a method for inhibiting TRPA1 activity, which generate little smell and effectively inhibit TRPA1 activity, an external preparation which gives low stimulation to skin, and an irritative sensation-mitigating agent which can effectively mitigate irritative sensation.

Means for Solving the Problem

The gist of the present invention relates to:

(1) a TRPA1 activity-inhibitor for inhibiting TRPA1 activity, which includes a compound represented by the formula (I):

[Chem. 1]

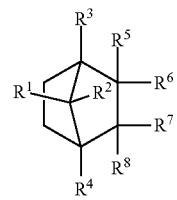

(I)

wherein each of $R^1$, $R^2$, $R^3$ and $R^4$ is independently hydrogen atom or methyl group, each of $R^5$, $R^6$, $R^7$ and $R^8$ is independently hydrogen atom, methyl group or a group represented by the formula (II):

$$-O-R^9-OH \qquad (II)$$

wherein $R^9$ is an alkylene group which may have a substituent;

with proviso that at least one group of $R^5$, $R^6$, $R^7$ and $R^8$ is a group represented by the formula (II);

(2) the TRPA1 activity-inhibitor according to the item (1), wherein $R^9$ is an alkylene group having 1 to 6 carbons which may have a substituent, in the group represented by the formula (II);

(3) a TRPA1 activity-inhibitor for inhibiting TRPA1 activity, which includes a compound represented by the formula (III):

[Chem. 2]

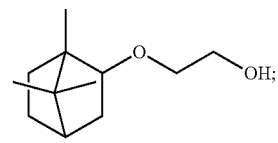

(III)

(4) a method for inhibiting TRPA1 activity, including a step of contacting with TRPA1 a compound represented by the formula (I):

[Chem. 3]

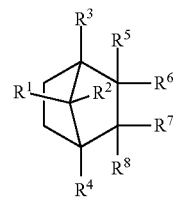

(I)

wherein each of $R^1$, $R^2$, $R^3$ and $R^4$ is independently hydrogen atom or methyl group, each of $R^5$, $R^6$, $R^7$ and $R^8$ is independently hydrogen atom, methyl group or a group represented by the formula (II):

—O—R$^9$—OH     (II)

wherein R$^9$ is an alkylene group which may have a substituent;
with proviso that at least one group of R$^5$, R$^6$, R$^7$ and R$^8$ is a group represented by the formula (II);
(5) the method for inhibiting TRPA1 activity according to the item (4), wherein R$^9$ is an alkylene group having 1 to 6 carbons which may have a substituent, in the group represented by the formula (II);
(6) the method for inhibiting TRPA1 activity according to the items (4) or (5), wherein the compound represented by the formula (I) is a compound represented by the formula (III):

[Chem. 4]

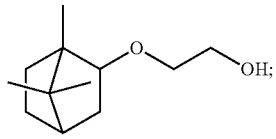

(III)

(7) an external preparation containing a component for activating TRPA1, including the TRPA1 activity-inhibitor according to any one of the items (1) to (3) as an active ingredient for inhibiting TRPA1 activation based on the component; and
(8) an irritative sensation-mitigating agent for mitigating irritative sensation caused by TRPA1 activation, which includes the TRPA1 activity-inhibitor according to any one of the items (1) to (3) as an active ingredient for mitigating irritative sensation caused by TRPA1 activation.

Effects of the Invention

The TRPA1 activity-inhibitor and the method for inhibiting TRPA1 activity of the present invention exhibit excellent effects such that the TRPA1 activity-inhibitor and the method generate little smell and effectively inhibit TRPA1 activity. Additionally, the external preparation of the present invention exhibits excellent effects such that the external preparation gives low unpleasant irritative sensation to skin. Furthermore, the irritative sensation-mitigating agent of the present invention exhibits excellent effects such that the irritative sensation-mitigating agent can effectively mitigate irritative sensation.

MODES FOR CARRYING OUT THE INVENTION

Figure 1:
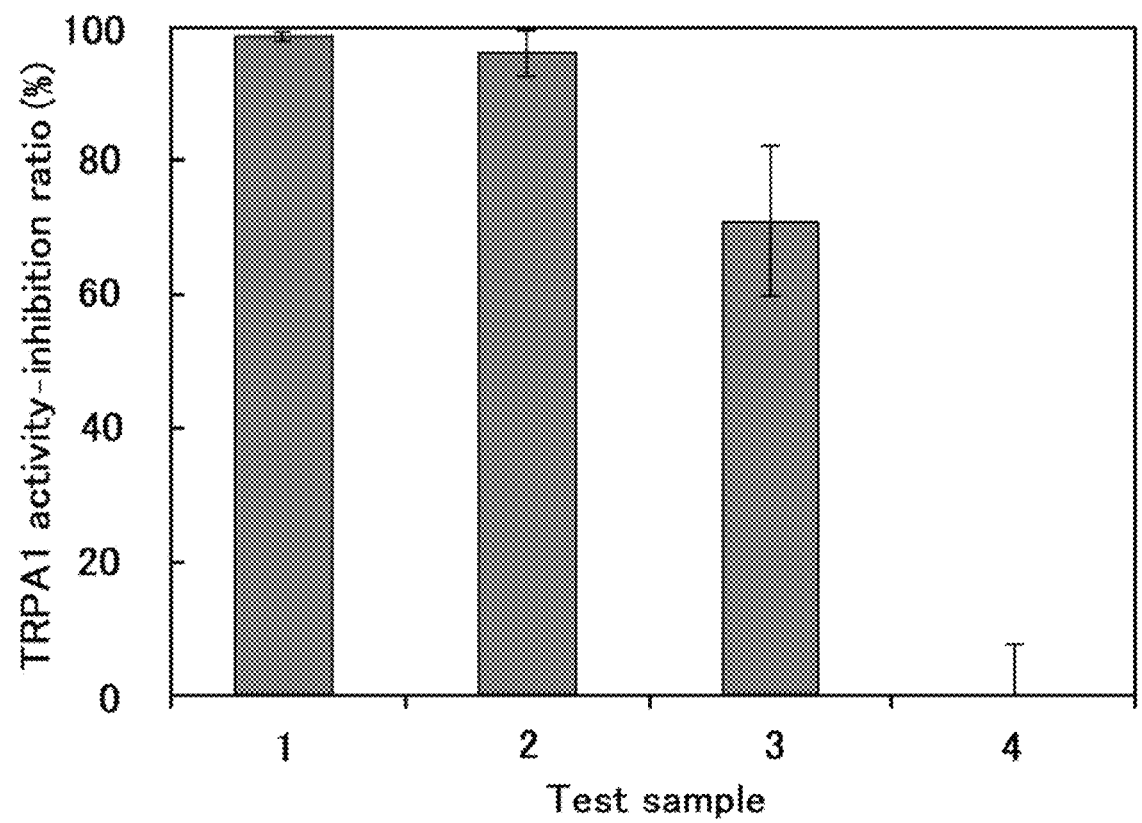
FIG. 1 is a graph showing results of examining the relationship between the kind of a test sample and the TRPA1 activity-inhibition ratio in Test Example 1.

1. TRPA1 Activity-Inhibitor
The TRPA1 activity-inhibitor of the present invention (hereinafter referred to as "activity-inhibitor") is an activity-inhibitor for inhibiting TRPA1 activity, which include a compound represented by the formula (I):

[Chem. 5]

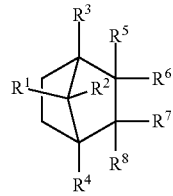

(I)

wherein each of R$^1$, R$^2$, R$^3$ and R$^4$ is independently hydrogen atom or methyl group, each of R$^5$, R$^6$, R$^7$ and R$^8$ is independently hydrogen atom, methyl group or a group represented by the formula (II):

—O—R$^9$—OH     (II)

wherein R$^9$ is an alkylene group which may have a substituent,
with proviso that at least one group of R$^5$, R$^6$, R$^7$ and R$^8$ is a group represented by the formula (II).

The compound represented by the formula (I) generates little smell, and inhibits TRPA1 activation based on a TRPA1 agonist, thereby inhibiting TRPA1 activity. Accordingly, since the TRPA1 activity-inhibitor of the present invention includes the compound represented by the formula (I), TRPA1 activity can be inhibited by contacting the TRPA1 activity-inhibitor with TRPA1.

In the formula (I), each of R$^1$, R$^2$, R$^3$ and R$^4$ is independently hydrogen atom or methyl group. Additionally, each of R$^5$, R$^6$, R$^7$ and R$^8$ is independently hydrogen atom, methyl group or a group represented by the formula (II). However, at least one group of R$^5$, R$^6$, R$^7$ and R$^8$ is a group represented by the formula (II). Furthermore, a carbon atom contained in the cyclohexane ring substituted with any one of groups of R$^3$ to R$^8$ can be an asymmetric carbon atom in some cases. The conformation of the compound represented by the formula (I) is not specifically limited. The conformation of the compound represented by the formula (I) can be any one of R-body, S-body and a mixture of R-body and S-body.

In the formula (II), R$^9$ is an alkylene group which may have a substituent. It is preferable that R$^9$ is an alkylene having 1 to 6 carbons which may have a substituent, from the viewpoint of sufficiently exhibiting an action of inhibiting TRPA1 activity (hereinafter also referred to as "TRPA1 activity-inhibiting action") and from the viewpoint of ensuring sufficient affinity for human skin in a case where the TRPA1 activity-inhibitor of the present invention is used for a human.

The carbon number of the alkylene group is preferably 1 or more, and more preferably 2 or more, from the viewpoint of sufficiently exhibiting the TRPA1 activity-inhibiting action. Additionally, the carbon number of the alkylene group is preferably 6 or less, and more preferably 4 or less, from the viewpoint of ensuring sufficient affinity for human skin in a case where the activity-inhibitor is used for a human.

The alkylene group having 2 or more carbons can be a straight-chain or a branched-chain. From the viewpoint of improving permeability to human skin, it is preferable that the alkylene group having 2 or more carbons has a straight chain. Additionally, the substituent which may be included in the alkylene group includes, for example, an alkenyl group having 2 to 6 carbons such as vinyl group, butenyl group, pentenyl group or hexenyl group; an aryl group having 6 to 12 carbons such as phenyl group or xylyl group; an aralkyl group having 7 to 12 carbons such as benzyl group or phenethyl group; an alkyl halide group having 1 to 4 carbons such as 3-chloropropyl group; an alkoxy group having 1 to 4 carbons such as methoxy group or ethoxy group; and the like, and the present invention is not limited only to those exemplified ones.

Among the compounds represented by the formula (I), a compound having the formula (I) in which each of $R^1$, $R^2$ and $R^3$ is methyl group and $R^6$ is —O—$CH_2$—$CH_2$—OH, that is, a compound represented by the following formula (III) is preferable, since the compound having the formula (I) in which each of $R^1$, $R^2$ and $R^3$ is methyl group and $R^6$ is —O—$CH_2$—$CH_2$—OH, that is, the compound represented by the following formula (III) has an especially weak smell, and can more effectively inhibit TRPA1 activity:

[Chem. 6]

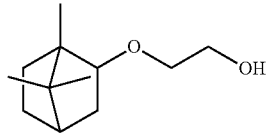

(III)

The compound represented by the formula (III) is a compound which is also called 2-isobornyloxyethanol, and which can be easily commercially available as an agent under the trade name of Cedanol Extra (CAS No. 7070-15-7).

The compounds represented by the formula (I) can be used alone or in combination of two or more kinds of compounds. Furthermore, the compound can be a racemic mixture.

The method for producing the compound represented by the formula (I) cannot be absolutely determined because the method for producing the compound represented by the formula (I) varies depending on the kind of the compound represented by the formula (I) and the like. It is therefore preferable to appropriately select the method in accordance with the kind of the compound represented by the formula (I). The method includes, for example, a production method including a step of isolating the compound represented by the formula (I) from an extract of a plant, a metabolite of a blue-green alga, and the like; a production method including a step of chemically synthesizing the compound represented by the formula (I); and the like, but the present invention is not limited to only such exemplification. The 2-isobornyloxyethanol can be produced by carrying out, for example, a procedure including the steps of reacting ethylene glycol with camphene in the presence of an acid catalyst such as p-toluenesulfonic acid, sulfuric acid, hydrochloric acid or an acidic ion-exchange resin, performing an aftertreatment by routine procedures, and then isolating the 2-isobornyloxyethanol by rectification method; and the like.

The content of the compound represented by the formula (I) in the activity-inhibitor of the present invention cannot be absolutely determined because the content of the compound represented by the formula (I) in the activity-inhibitor of the present invention varies depending on the kind of the compound represented by the formula (I), the use of the activity-inhibitor of the present invention and the like. It is therefore preferable to appropriately set the content in accordance with the kind of the compound represented by the formula (I), the use of the activity-inhibitor of the present invention and the like. The content of the compound represented by the formula (I) in the activity-inhibitor of the present invention is preferably 0.0001% by mass or more, more preferably 0.001% by mass or more, even more preferably 0.01% by mass or more, from the viewpoint of sufficiently exhibiting the TRPA1 activity-inhibiting action, and 100% by mass or less, from the viewpoint of ensuring sufficient affinity for human skin.

The activity-inhibitor of the present invention can include other components such as water, a pH conditioner, a chelating agent and a stabilizer, within a range which would not hinder an object of the present invention. Additionally, when the activity-inhibitor of the present invention includes other components, the compound represented by the formula (I) and other components can form a complex in the activity-inhibitor of the present invention within a range which would not hinder an object of the present invention.

The activity-inhibitor of the present invention can have an action of enhancing TRPM8 activity involved in cold sensation in skin (hereinafter referred to as "TRPM8 activity-enhancing action") in some cases, depending on the content thereof and the like. Since the activity-inhibitor of the present invention has the TRPM8 activity-enhancing action depending on the content thereof and the like, the activity-inhibitor of the present invention can give cold sensation to skin. Accordingly, the activity-inhibitor of the present invention can exhibit both of an effect of suppress unpleasant irritative sensation caused by TRPA1 activation and an effect of giving cold sensation to skin.

Additionally, since the activity-inhibitor of the present invention inhibits TRPA1 activity relevant to unpleasant irritative sensation in skin, the activity-inhibitor of the present invention can suppress unpleasant irritative sensation in skin. Accordingly, the activity-inhibitor of the present invention can be used as an irritative sensation-mitigating agent for mitigating irritative sensation caused by TRPA1 activation.

The TRPA1 is one of transient receptor potential channels (TRP channels) each expressing functions as an irritant receptor. The amino acid sequence of the TRPA1 is shown in SEQ ID NO: 2 (GenBank Accession No. NM_007332). Additionally, in the present invention, TRPA1 can be a variant of a polypeptide consisting of the amino acid sequence shown in SEQ ID NO: 2, as long as the polypeptide exhibits an activity equivalent to the activity of a polypeptide consisting of the amino acid sequence shown in SEQ ID NO: 2 (hereinafter referred to as "TRPA1 activity"). The variant includes, for example, (A) a polypeptide having substitution, deletion or insertion of 1 or several amino acid residues in the sequence shown in SEQ ID NO: 2 and exhibiting the TRPA1 activity; (B) a polypeptide consisting of an amino acid sequence of which sequence identity to the sequence shown in SEQ ID NO: 2 is 80% or more and exhibiting the TRPA1 activity; and the like, and the present invention is not limited only to those exemplified ones. Additionally, in the item (A), the term "1 or several" refers to 1 to 30, preferably 1 to 20, more preferably 1 to 10, even more preferably 1 to 3, and especially preferably 1 or 2. Furthermore, the "sequence identity" refers to a value calculated by aligning the amino acid sequence of the evaluation target (query sequence) to the amino acid sequence shown in SEQ ID NO: 2 (reference sequence) with the use of PROTEIN BLAST based on BLAST algorithm under default conditions [Expect threshold: 10, word size: 3, Gap Costs (Existence 11, Extension 1) and Matrix: BLSUM62].

In the item (B), the sequence identity can be any value as long as the sequence identity is within the range in which the polypeptide exhibits the TRPA1 activity. The sequence identity is 80% or more, preferably 90% or more, more preferably 95% or more, even more preferably 98% or more, and especially preferably 100%.

The TRPA1 activity includes, for example, an ability of controlling an ion flux in a cell, an ability of controlling membrane potential in a cell, and the like, and the present invention is not limited only to those exemplified ones. The ability of controlling an ion flux in a cell includes, for example, an ability of transporting positive ions from the outside of a cell to the inside of the cell, and the like, and the present invention is not limited only to those exemplified ones. Additionally, the ability of controlling membrane potential in a cell includes, for example, an ability of generating a current, and the like, and the present invention is not limited only to those exemplified ones. TRPA1 activity is exhibited by binding a TRPA1 agonist to TRPA1, thereby activating the TRPA1. The positive ion includes, for example, calcium ion, sodium ion, and the like, and the present invention is not limited only to those exemplified ones.

The TRPA1 agonist includes, for example, menthol, ethanol, 1,3-butylene glycol, propylene glycol, an alkali agent (for example, ammonia, monoethanolamine, potassium hydroxide, or the like), allyl isothiocyanate, methylparaben, allysine, icilin, hydrogen peroxide, bradykinin, acrolein, a perfumed oil component (for example, citral, eugenol, cinnamaldehyde, or the like), and the like, and the present invention is not limited only to those exemplified ones.

The TRPA1 activity-inhibiting action of the activity-inhibitor of the present invention can be evaluated on the basis of, for example, the calcium ion concentration in a cell expressing TRPA1 (hereinafter referred to as "TRPA1-expressing cell"), a current in a TRPA1-expressing cell, and the like.

When the calcium ion concentration in a TRPA1-expressing cell is used, the TRPA1 activity-inhibiting action can be evaluated by carrying out, for example, the following steps:
(A1) contacting a TRPA1-expressing cell with a test substance (an activity-inhibitor) and a TRPA1 agonist, and measuring the calcium ion concentration in the TRPA1-expressing cell [referred to as "calcium ion concentration (A)"],
(A2) contacting a TRPA1-expressing cell with a TRPA1 agonist, and measuring the calcium ion concentration in the TRPA1-expressing cell [referred to as "calcium ion concentration (B)"], and
(A3) comparing the calcium ion concentration (A) obtained in the step (A1) with the calcium ion concentration (B) obtained in the step (A2)
(referred to as "evaluation method A"). In the step (A3), when the calcium ion concentration (A) is decreased as compared with the calcium ion concentration (B), it can be evaluated that the test substance has the TRPA1 activity-inhibiting action. Additionally, it can be evaluated that the test substance has higher TRPA1 activity-inhibiting action when the difference between the calcium ion concentration (A) and the calcium ion concentration (B) is larger.

The calcium ion concentration can be measured by, for example, a method including the steps of introducing a calcium chelating agent-based fluorescence reagent (hereinafter also referred to as "fluorescent calcium indicator") into a TRPA1-expressing cell, binding the fluorescent calcium indicator to a calcium ion in the cell, and examining the fluorescence intensity of the fluorescent calcium indicator bound to a calcium ion. The fluorescent calcium indicator can be any reagent, as long as the reagent binds to a calcium ion and shows change in the fluorescence property depending on the amount of the fluorescent calcium indicator. The fluorescent calcium indicator includes, for example, Fura 2, Fura 2-AM, Fluo-3, Fluo-4 and the like, and the present invention is not limited only to those exemplified ones.

When a current in a TRPA1-expressing cell is used, the TRPA1 activity-inhibiting action can be measured by carrying out, for example, the following steps:
(B1) contacting a TRPA1-expressing cell with a test substance (an activity-inhibitor) and a TRPA1 agonist, and measuring a current under constant potential in the TRPA1-expressing cell [referred to as "current (A)"],
(B2) contacting a TRPA1-expressing cell with a TRPA1 agonist, and measuring the current under the same potential as the potential used in the step (B1) in the TRPA1-expressing cell [referred to as "current B"], and
(B3) comparing the current (A) obtained in the step (B1) with the current (B) obtained in the step (B2)
(referred to as "evaluation method B"). In the step (B3), when the current (B) is lower than the current (A), it can be evaluated that the test substance has the TRPA1 activity-inhibiting action. Additionally, it can be evaluated that the test substance has higher TRPA1 activity-inhibiting action when the difference between the current (A) and the current (B) is larger. The current can be measured by a patch-clamp method and the like.

2. Method for Inhibiting TRPA1 Activity

The compound represented by the formula (I) can inhibit TRPA1 activity. The method for inhibiting TRPA1 activity of the present invention (hereinafter referred to as "activity-inhibition method") is a method for inhibiting TRPA1 activity, including a step of contacting the compound represented by the formula (I) with TRPA1.

The activity-inhibition method of the present invention enables to effectively inhibit activity of TRPA1 such as TRPA1 contained in a sensory nerve present in human skin or TRPA1 contained in a sensory nerve present under mucosa of oral cavity, and the like, since the compound represented by the formula (I) is used.

Among the compounds represented by the formula (I), a compound represented by the formula (I) in which each of $R^1$, $R^2$ and $R^3$ is methyl group and $R^6$ is —O—$CH_2$—$CH_2$—OH, that is, a compound represented by the formula (III) (2-isobornyloxyethanol) is preferable, since the compound can more effectively inhibit TRPA1 activity and generates a weak smell.

The compound represented by the formula (I) can be contacted with TRPA1 by, for example, supplying the compound represented by the formula (I) to a part containing TRPA1, for example, a cell which constitutes skin, and the like.

The amount of the compound represented by the formula (I) to be contacted with TRPA1 cannot be absolutely determined because the amount of the compound represented by the formula (I) to be contacted with TRPA1 varies depending on the object for application of the activity-inhibition method of the present invention, and the like. It is therefore preferable to appropriately set the amount of the compound represented by the formula (I) to be contacted with TRPA1 in accordance with the object for application of the activity-inhibition method of the present invention, and the like. In general, when the object for application of the activity-inhibition method of the present invention is TRPA1 contained in a sensory nerve present in skin, the amount of the compound represented by the formula (I) to be contacted with TRPA1 is, for example, preferably 10 μg or more per 10 cm² of skin, and more preferably 100 μg or more per 10 cm² of skin, from the viewpoint of sufficiently exhibiting the TRPA1 activity-inhibiting action, and preferably 100 mg or less per 10 cm² of skin, and more preferably 10 mg or less per 10 cm² of skin, from the viewpoint of suppressing a load on skin.

The TRPA1 activity-inhibiting action exhibited by the activity-inhibition method of the present invention can be evaluated in the same manner as in evaluation of the TRPA1 activity-inhibiting action of the activity-inhibitor.

The activity-inhibition method of the present invention can inhibit TRPA1 activity relevant to unpleasant irritative sensation in skin. Accordingly, for example, when an external preparation including a component which can give unpleasant irritative sensation caused by TRPA1 activation upon contacting the component with skin is used, activity of TRPA1 contained in the cell in skin can be inhibited by carrying out the activity-inhibition method using the compound represented by the formula (I) and the external preparation in combination, to suppress the unpleasant irritative sensation caused by TRPA1 activation. Accordingly, the activity-inhibition method of the present invention is suitable for application when a human with sensitive skin uses an external preparation including a component which can give unpleasant irritative sensation caused by TRPA1 activation.

3. External Preparation

In one aspect, the external preparation of the present invention is an external preparation containing a component for activating TRPA1, including the TRPA1 activity-inhibitor as an active ingredient for inhibiting TRPA1 activation based on the component (hereinafter referred to as "the external preparation of Embodiment 1"). Since the TRPA1 activity-inhibitor inhibits TRPA1 activity relevant to unpleasant irritative sensation in skin, the TRPA1 activity-inhibitor can suppress unpleasant irritative sensation in skin caused by TRPA1 activation. Since the external preparation of Embodiment 1 includes the TRPA1 activity-inhibitor, the external preparation can reduce unpleasant irritative sensation caused by TRPA1 activation such as unpleasant irritative sensation caused by a component for activating TRPA1 contained in the external preparation. The external preparation of Embodiment 1 is preferably an external preparation for sensitive skin.

In the present specification, "sensitive skin" refers to skin which has reduced skin barrier function and which tends to sensitively react to a substance, stimulation and the like to which average skin does not react and tends to cause a state such as sensation of itchiness of skin or dryness and roughness of skin.

Additionally, in the present specification, "a component for activating TRPA1" refers to a component which can be used for an external preparation, among the TRPA1 agonists. The component for activating TRPA1 includes, for example, a component which shows that the calcium ion concentration (A) is increased as compared with the calcium ion concentration (B) in the step (A3) of the evaluation method A when the same procedures as those in the evaluation method A were carried out; a component which exhibits the current (A) higher than the current (B) in the step (B3) of the evaluation method B when the evaluation method B was carried out; and the like, and the present invention is not limited only to those exemplified ones. The component for activating TRPA1 includes, for example, menthol, ethanol, 1,3-butylene glycol, propylene glycol, an alkali agent (for example, ammonia, monoethanolamine, potassium hydroxide, or the like), allyl isothiocyanate, methylparaben, allysine, icilin, hydrogen peroxide, bradykinin, acrolein, a perfumed oil component (for example, citral, eugenol, cinnamaldehyde, or the like) and the like, and the present invention is not limited only to those exemplified ones.

Among the compounds represented by the formula (I) included in the activity-inhibitor in the external preparation of Embodiment 1, a compound having the formula (I) in which each of $R^1$, $R^2$ and $R^3$ is methyl group and $R^6$ is —O—$CH_2$—$CH_2$—OH, that is, a compound represented by the formula (III) (2-isobornyloxyethanol) is preferable, since the compound can more effectively inhibit TRPA1 activity and generate a weak smell.

The content of the activity-inhibitor in the external preparation of Embodiment 1 cannot be absolutely determined because the content of the activity-inhibitor in the external preparation of Embodiment 1 varies depending on the kind and the amount of the component for activating TRPA1, the kind of the TRPA1 activity-inhibitor, the use of the external preparation, and the like. It is therefore preferable to appropriately set the content in accordance with the kind and the amount of the component for activating TRPA1, the kind of the TRPA1 activity-inhibitor, the use of the external preparation, and the like. In general, it is desirable that the content of the activity-inhibitor in the external preparation of Embodiment 1 is controlled so that the content of the compound represented by the formula (I) in the external preparation of Embodiment 1 become preferably 0.01% by mass or more, more preferably 0.05% by mass or more, even more preferably 0.08% by mass or more, and especially preferably 0.1% by mass or more, from the viewpoint of suppressing unpleasant irritative sensation caused by the component for activating TRPA1, and preferably 8% by mass or less, and more preferably 5% by mass or less, from the viewpoint of suppressing the load on skin.

The amount of the activity-inhibitor relative to the component for activating TRPA1 cannot be absolutely determined because the amount of the activity-inhibitor relative to the component for activating TRPA1 varies depending on the kind and the amount of the components for activating TRPA1, the kind of the TRPA1 activity-inhibitor, the use of the external preparation, and the like. It is therefore preferable to appropriately set the amount in accordance with the kind and the amount of the component for activating TRPA1, the kind of the TRPA1 activity-inhibitor, the use of the external preparation, and the like. In general, it is desirable that the amount of the activity-inhibitor relative to the component for activating TRPA1 is controlled so that the amount of the compound represented by the formula (I) per 100 parts by mass of the component for activating TRPA1 become preferably 1 part by mass or more, and more preferably 10 parts by mass or more, from the viewpoint of suppressing unpleasant irritative sensation caused by the component for activating TRPA1, and preferably 500 parts by mass or less, and more preferably 200 parts by mass or less, from the viewpoint of moderately exhibiting the desired action of the component for activating TRPA1.

In addition to the "component for activating TRPA1", the external preparation of Embodiment 1 can contain a component exemplified by an oiling agent such as higher alcohol other than the component for activating TRPA1, wax, hydrocarbon oil, a fatty acid, oil and fat, ester oil or silicone oil; a surfactant such as an anionic surfactant, a cationic surfactant, a nonionic surfactant or an amphoteric surfactant; a moisturizer such as polyhydric alcohol other than the component for activating TRPA1, sugar, hyaluronic acid or a hyaluronic acid derivative; a thickener; an antioxidant; a chelating agent; a pH-adjuster other than the component for activating TRPA1; a perfume other than the component for activating TRPA1; a pigment; a ultraviolet absorber; a ultraviolet scattering agent; a vitamin; an amino acid; an antiseptic other than the component for activating TRPA1; water; or the like, within a range which would not hinder an object of the present invention.

When the compound represented by the formula (I) included in the activity-inhibitor is 2-isobornyloxyethanol, the activity-inhibitor can suppress unpleasant irritative sensation caused by TRPA1 activation, and can give cool sensation caused by TRPM8 activation to human skin. Accordingly, the activity-inhibitor including 2-isobornyloxyethanol can be used as a cooling agent in place of the component for activating TRPA1 such as menthol, in the external preparation of Embodiment 1.

The dosage form of the external preparation of Embodiment 1 can be appropriately selected depending on the use of the external preparation, and the like. The dosage form of the external preparation includes, for example, lotion, cream, foam, emulsion, gel, a pack, powder, an aerosol agent, a skin patch, and the like, and the present invention is not limited only to those exemplified ones.

The external preparation of Embodiment 1 encompasses an external preparation for skin such as a cosmetic to be directly applied to skin, an external preparation for scalp hair which may contact with skin in some cases, and the like.

The external preparation for skin includes, for example, body lotion, a deodorant cosmetic (for example, deodorant lotion, deodorant gel, deodorant spray, a roll-on deodorant cosmetic, deodorant paper, or the like), skin lotion, emulsion, skin care cream, a tonic, a stick cosmetic, lip balm, a skin bleaching agent (a body bleaching agent), a cleansing agent (for example, shower gel, a makeup remover, face wash, solid soap, or the like), a sheet cosmetic (for example, wiping sheet, a sheet pack, or the like), a skin patch (for example, a poultice, or the like), a cosmetic for shaving (for example, shaving gel, or the like), and the like, and the present invention is not limited only to those exemplified ones.

Additionally, the external preparation for scalp hair includes, for example, a cosmetic for washing hair (for example, shampoo, rinse, or the like), a hair growth agent, hair dye, hair bleach, perm solution, a hairstyling agent (for example, hair tonic, or the like), and the like, and the present invention is not limited only to those exemplified ones.

As explained above, since the external preparation of Embodiment 1 can reduce unpleasant irritative sensation in human skin, the external preparation is useful as an external preparation for sensitive skin which is sensitive to unpleasant irritative sensation.

In another aspect, the external preparation of the present invention is an external preparation containing at least one kind of component selected from the group consisting of menthol, ethanol, 1,3-butylene glycol, propylene glycol, an alkali agent, allyl isothiocyanate, methylparaben, allysine, icilin, hydrogen peroxide, bradykinin, acrolein, citral, eugenol and cinnamaldehyde, including the compound represented by the formula (I) as an active ingredient for suppressing stimulation based on the component, in which the content of the compound represented by the formula (I) is 0.01 to 8% by mass (hereinafter also referred to as "external preparation of Embodiment 2"). Since the external preparation of Embodiment 2 includes the compound represented by the formula (I), stimulation based on the component contained in the external preparation can be reduced. Accordingly, the external preparation of Embodiment 2 can be used as an external preparation for sensitive skin, as with the external preparation of Embodiment 1.

Among the compounds represented by the formula (I) included in the external preparation of Embodiment 2, a compound having the formula (I) in which each of $R^1$, $R^2$ and $R^3$ is methyl group and $R^6$ is —O—$CH_2$—$CH_2$—OH, that is, a compound represented by the formula (III) (2-isobornyloxyethanol) is preferable, since the compound can more effectively suppress stimulation based on the component and has an especially weak smell.

The content of the compound represented by the formula (I) in the external preparation of Embodiment 2 is 0.01% by mass or more, preferably 0.05% by mass or more, more preferably 0.08% by mass or more, and even more preferably 0.1% by mass or more, from the viewpoint of sufficiently exhibiting an action inhibiting stimulation based on the component, and 8% by mass or less, and preferably 5% by mass or less, from the viewpoint of suppressing a load on skin.

The amount of the compound represented by the formula (I) per 100 parts by mass of the component cannot be absolutely determined because the amount of the compound represented by the formula (I) per 100 parts by mass of the component varies depending on the kind and the amount of the component, the kind of the compound represented by the formula (I), the use of the external preparation, and the like. It is therefore preferable to appropriately set the amount in accordance with the kind and the amount of the component, the kind of the compound represented by the formula (I), the use of the external preparation, and the like. In general, the amount of the compound represented by the formula (I) per 100 parts by mass of the component is preferably 1 part by mass or more, and more preferably 10 parts by mass or more, from the viewpoint of suppressing stimulation based on the component, and preferably 500 parts by mass or less, and more preferably 200 parts by mass or less, from the viewpoint of moderately exhibiting the desired action of the component.

In addition to the component, the external preparation of Embodiment 2 can contain a component exemplified by an oiling agent such as higher alcohol, wax, hydrocarbon oil, a fatty acid, oil and fat, ester oil or silicone oil; a surfactant such as an anionic surfactant, a cationic surfactant, a nonionic surfactant or an amphoteric surfactant; a moisturizer such as polyhydric alcohol, sugar, hyaluronic acid or a hyaluronic acid derivative; a thickener; an antioxidant; a chelating agent; a pH-adjuster; a perfume; a pigment; a ultraviolet absorber; a ultraviolet scattering agent; a vitamin; an amino acid; an antiseptic; water; or the like, within a range which would not hinder an object of the present invention.

The dosage form of the external preparation of Embodiment 2 is the same dosage as that of the external preparation of Embodiment 1. The external preparation of Embodiment 2 encompasses an external preparation for skin such as a cosmetic to be directly applied to skin, an external preparation for scalp hair which may contact with skin in some cases, and the like, as with the external preparation of Embodiment 1.

As explained above, since the external preparation of Embodiment 2 can reduce unpleasant irritative sensation in human skin by the component, the external preparation is useful as an external preparation for sensitive skin which is sensitive to unpleasant irritative sensation.

4. Irritative Sensation-Mitigating Agent

Since the activity-inhibitor of the present invention inhibits TRPA1 activity relevant to unpleasant irritative sensation in skin, the activity-inhibitor of the present invention can suppress unpleasant irritative sensation in skin. Accordingly, the activity-inhibitor of the present invention can be used for mitigation of irritative sensation caused by TRPA1 activation.

The irritative sensation-mitigating agent of the present invention is an irritative sensation-mitigating agent for mitigating irritative sensation caused by TRPA1 activation, which includes the TRPA1 activity-inhibitor as an active ingredient for mitigating irritative sensation caused by TRPA1 activation. Since the irritative sensation-mitigating agent of the present invention includes the TRPA1 activity-inhibitor, the irritative sensation-mitigating agent of the present invention can mitigate irritative sensation caused by TRPA1 activation.

The content of the TRPA1 activity-inhibitor in the irritative sensation-mitigating agent of the present invention cannot be absolutely determined because the content of the TRPA1 activity-inhibitor in the irritative sensation-mitigating agent of the present invention varies depending on the kind and the amount of the component for activating TRPA1, the kind of the TRPA1 activity-inhibitor, the use of the agent for mitigating stimulation, and the like. It is therefore preferable to appropriately set the content of the TRPA1 activity-inhibitor in the irritative sensation-mitigating agent of the present invention in accordance with the kind and the amount of the component for activating TRPA1, the kind of the TRPA1 activity-inhibitor, the use of the agent for mitigating stimulation, and the like. In general, the content of the activity-inhibitor in the agent for mitigating stimulation of the present invention is preferably 0.0001% by mass or more, more preferably 0.001% by mass or more, and even more preferably 0.01% by mass or more as the content of the compound represented by the formula (I) in the agent for mitigating stimulation of the present invention, from the viewpoint of mitigating the irritative sensation caused by TRPA1 activation, and preferably 100% by mass or less as the content of the compound represented by the formula (I) in the agent for mitigating stimulation of the present invention, from the viewpoint of ensuring affinity for human skin.

The irritative sensation-mitigating agent of the present invention can contain a component exemplified by an oiling agent such as higher alcohol, wax, hydrocarbon oil, a fatty acid, oil and fat, ester oil or silicone oil; a surfactant such as an anionic surfactant, a cationic surfactant, a nonionic surfactant or an amphoteric surfactant; a moisturizer such as polyhydric alcohol, sugar, hyaluronic acid or a hyaluronic acid derivative; a thickener; an antioxidant; a chelating agent; a pH-adjuster; a perfume; a pigment; a ultraviolet absorber; a ultraviolet scattering agent; a vitamin; an amino acid; an antiseptic; water; or the like, within a range which would not hinder an object of the present invention.

EXAMPLES

The present invention will be explained in more detail in Examples below, but the present invention is not limited to such Examples.

Example 1

In a solvent A [composition: 140 mM sodium chloride, 5 mM potassium chloride, 2 mM magnesium chloride, 2 mM calcium chloride, 10 mM glucose and 10 mM HEPES hydrochloric acid buffer (pH 7.4)], 2-isobornyloxyethanol [manufactured by TAKASAGO INTERNATIONAL CORPORATION under the trade name of Cedanol, CAS No.: 7070-15-7] was dissolved at 25° C. so that the concentration of 2-isobornyloxyethanol became 1 mM, to obtain a TRPA1 activity-inhibitor.

Reference Example 1

Borneol [manufacture by Wako Pure Chemical Corporation] was dissolved in a solvent A [composition: 140 mM sodium chloride, 5 mM potassium chloride, 2 mM magnesium chloride, 2 mM calcium chloride, 10 mM glucose and 10 mM HEPES hydrochloric acid buffer (pH 7.4)] at 25° C. so that the concentration of borneol became 1 mM, to obtain a sample.

Reference Example 2

A sample was obtained in the same manner as in Reference Example 1 except that 1,8-cineole was used in place of borneol.

Comparative Example 1

Glycerol was dissolved in a solvent A [composition: 140 mM sodium chloride, 5 mM potassium chloride, 2 mM magnesium chloride, 2 mM calcium chloride, 10 mM glucose and 10 mM HEPES hydrochloric acid buffer (pH 7.4)] at 25° C. so that the concentration of glycerol became 5 mM, to obtain a sample.

Preparation Example 1 (Preparation of TRPA1-Expressing Cell)

A cDNA encoding human TRPA1 [a polynucleotide of position 63 to position 3888 of the nucleotide sequence shown in SEQ ID NO: 1 (GenBank Accession No.: NM_007332)] was inserted into a cloning site of a vector for mammalian cells [manufactured by Invitrogen under the trade name of pcDNA3.1(+)], to obtain a human TRPA1-expression vector. One microgram of the resulting human TRPA1-expression vector was mixed with 6 µL of a gene transfer reagent [manufactured by Invitrogen under the trade name of PLUS Reagent, Catalogue No.: 11514-015], to obtain a mixture I. Additionally, 4 µL of a cationic lipid for gene transfer [manufactured by Invitrogen under the trade name of Lipofectamine (registered trademark), Catalogue No.: 18324-012] was mixed with 200 µL of a medium for reducing serum consumption [Manufactured by Invitrogen under the trade name of Opti-MEM (registered trademark) I Reduced Serum Medium (catalogue No.: 11058021)], to obtain a mixture II.

Furthermore, $5 \times 10^5$ cells of HEK293 cells were cultured in a 10% by mass fetal bovine serum (FBS)-containing Dulbecco's modified Eagle's medium (DMEM) on a dish having a diameter of 35 mm maintained at 37° C. under 5% by volume carbon dioxide atmosphere to 70% confluence.

By adding the mixture I and the mixture II to the resulting cell culture, the human TRPA1-expression vector was introduced into HEK293 cells, to obtain TRPA1-expressing cells.

Preparation Example 2 (Production of TRPA8-Expressing Cell)

A cDNA encoding human TRPM8 [a polynucleotide of position 41 to position 3355 of the nucleotide sequence shown in SEQ ID NO: 3 (GenBank Accession No.: NM_024080)] was inserted into a cloning site of a vector for mammalian cells [manufactured by Invitrogen under the trade name of pcDNA3.1(+)], to obtain a human TRPM8-expression vector. One microgram of the resulting human TRPM8-expression vector was mixed with 6 μL of a gene transfer reagent [manufactured by Invitrogen under the trade name of PLUS Reagent, Catalogue No.: 11514-015], to obtain a mixture III. Additionally, 4 μL of a cationic lipid for gene transfer [manufactured by Invitrogen under the trade name of Lipofectamine (registered trademark), Catalogue No.: 18324-012] was mixed with 200 μL of a medium for reducing serum consumption [Manufactured by Invitrogen under the trade name of Opti-MEM (registered trademark) I Reduced Serum Medium (Catalogue No.: 11058021)] as with Preparation Example 1, to obtain a mixture II.

Furthermore, $5 \times 10^5$ cells of HEK293 cells were cultured in a 10% by mass FBS-containing DMEM on a dish having a diameter of 35 mm maintained at 37° C. under 5% by volume carbon dioxide atmosphere to 70% confluence.

Human TRPM8-expression vector was introduced into the HEK293 cell by adding the mixture III and the mixture II to the resulting cell culture, to obtain a TRPM8-expressing cell.

Test Example 1

The TRPA1-expressing cells obtained in Preparation Example 1 were incubated in a 10% by mass FBS-containing DMEM medium containing a reagent for measuring calcium ion in a cell, Fura 2-AM (manufactured by Invitrogen) at a final concentration of 5 μM at room temperature for 60 minutes, thereby introducing Fura 2-AM into the TRPA1-expressing cells, to obtain Fura 2-AM-introduced TRPA1-expressing cells.

The resulting Fura 2-AM-introduced TRPA1-expressing cells were put into each chamber of a fluorometric apparatus equipped with circulating thermostatic chambers [manufactured by Hamamatsu Photonics K.K. under the trade name of ARGUS-50]. Thereafter, the Fura 2-AM-introduced TRPA1-expressing cells in the chamber were washed with a solvent A [composition: 140 mM sodium chloride, 5 mM potassium chloride, 2 mM magnesium chloride, 2 mM calcium chloride, 10 mM glucose and 10 mM HEPES hydrochloric acid buffer (pH 7.4)]

Next, a TRPA1 agonist was put into the chamber containing the resulting Fura 2-AM-introduced TRPA1-expressing cells after washing, thereby mixing the Fura 2-AM-introduced TRPA1-expressing cells with the agonist. As the agonist, a solvent A containing 1 mM menthol was used.

Thereafter, intensity of fluorescence A based on the Fura 2-AM introduced into the TRPA1-expressing cell and bound to a calcium ion in the cells at an excitation wavelength of 340 nm in the chamber and intensity of fluorescence B based on the Fura 2-AM introduced into the TRAP1-expressing cell at an excitation wavelength of 380 nm were measured.

Using the measured intensity of fluorescence A and B, $\Delta$fluorescence intensity ratio$_{agonist}$ was calculated. The $\Delta$fluorescence intensity ratio$_{agonist}$ was calculated on the basis of the formula (IV):

[Formula 1]

$\Delta$Fluorescence intensity ratio$_{agonist}$=(Fluorescence intensity$_{340\ nm}$ in the presence of an agonist/ Fluorescence intensity 380 nm in the presence of an agonist)−(Fluorescence intensity$_{340\ nm}$ in the presence of a control/Fluorescence intensity$_{380\ nm}$ in the presence of a control) (IV).

In the formula (IV), the intensity of fluorescence A was used as fluorescence intensity$_{340\ nm}$, and the intensity of fluorescence B was used as fluorescence intensity$_{380\ nm}$. In the formula (IV), the control is a solvent A.

Additionally, the same procedures as those of the case where the agonist was used alone were carried out except that the TRPA1 activity-inhibitor obtained in Example 1, the sample obtained in Reference Example 1, the sample obtained in Reference Example 2 or the sample obtained in Comparative Example 1 was used as a test sample in mixture with the agonist in place of the agonist alone, and thereafter intensity of fluorescence C based on the Fura 2-AM introduced into the TRPA1-expressing cell and bound to a calcium ion in the cell at an excitation wavelength of 340 nm and intensity of fluorescence D based on the Fura 2-AM introduced into the TRPA1-expressing cell at an excitation wavelength of 380 nm were measured.

Using measured intensity of fluorescence C and D, $\Delta$fluorescence intensity ratio$_{test\ sample}$ was calculated. The $\Delta$Fluorescence intensity ratio$_{test\ sample}$ was calculated on the basis of the formula (V):

[Formula 2]

$\Delta$Fluorescence intensity ratio$_{test\ sample}$=(Fluorescence intensity$_{340\ nm}$ in the presence of a test sample/ Fluorescence intensity$_{380\ nm}$ in the presence of a test sample)−(Fluorescence intensity$_{340\ nm}$ in the presence of a control/Fluorescence intensity$_{380\ nm}$ in the presence of a control) (V).

In the formula (V), the intensity of fluorescence C was used as fluorescence intensity$_{340\ nm}$, and the intensity of fluorescence D was used as fluorescence intensity$_{380\ nm}$. In the formula (V), the control is a solvent A.

Using the calculated $\Delta$fluorescence intensity ratio$_{agonist}$ and $\Delta$fluorescence intensity ratio$_{test\ sample}$, inhibition ratio to TRPA1 activity (TRPA1 activity-inhibition ratio) was calculated. On the basis of the formula (VI);

[Formula 3]

TRPA1 activity-inhibition ratio (%)=($\Delta$Fluorescence intensity ratio$_{agonist}$−$\Delta$Fluorescence intensity ratio$_{test\ sample}$)/$\Delta$Fluorescence intensity ratio$_{agonist}$ (VI), the TRPA1 activity-inhibition ratio was calculated.

The results of examining the relationship between the kind of test samples and TRPA1 activity-inhibition ratio in Test Example 1 are shown in FIG. 1. In the figure, lane 1 shows TRPA1 activity-inhibition ratio in the case where the TRPA1 activity-inhibitor obtained in Example 1 was used as a test sample; lane 2 shows TRPA1 activity-inhibition ratio in the case where the sample obtained in Reference Example 1 was used as a test sample; lane 3 shows TRPA1 activity-inhibition ratio in the case where the sample obtained in Reference Example 2 was used as a test sample; and lane 4 shows TRPA1 activity-inhibition ratio in the case where the sample obtained in Comparative Example 1 was used as a test sample.

From the results shown in FIG. 1, it can be seen that the TRPA1 activity-inhibition ratio in the case where the TRPA1 activity-inhibitor obtained in Example 1 was used (in FIG. 1, lane 1) is about 99%. Additionally, it can be seen that the TRPA1 activity-inhibition ratio in the case where the TRPA1 activity-inhibitor obtained in Reference Example 1 is used (in FIG. 1, lane 2) and the TRPA1 activity-inhibition ratio in the case where the TRPA1 activity-inhibitor obtained in Reference Example 2 (in FIG. 1, lane 3) are about 96% and about 71%, respectively. On the other hand, since the TRPA1 activity-inhibition ratio in the case where the sample obtained in Comparative Example 1 containing glycerol as a control (in FIG. 1, lane 4) was 0% or less, it is suggested that 2-isobornyloxyethanol contained in the activity-inhibitor obtained in Example 1 acts as a blocker and inhibits TRPA1 activity exhibited by TRPA1 activation caused by menthol. Additionally, it can be seen that 2-isobornyloxyethanol contained in the activity-inhibitor obtained in Example 1 inhibits TRPA1 activity as with borneol and 1,8-cineole.

Furthermore, when the compound represented by the formula (I) other than 2-isobornyloxyethanol was used as the compound represented by the formula (I), the same tendency as that of the case where 2-isobornyloxyethanol was used can be seen. The compound represented by the formula (I) is a compound generating a weak smell. From these results, it can be seen that the compound represented by the formula (I) has a weak smell and effectively inhibits TRPA1 activity. Thus, the compound represented by the formula (I) can be used as a TRPA1 activity-inhibitor. Additionally, the compound represented by the formula (I) can suppress unpleasant irritative sensation caused by TRPA1 activation based on a component for activating TRPA1 in an external preparation containing the component. Accordingly, the compound represented by the formula (I) can be used as an active ingredient in an external preparation containing a component for activating TRPA1. Furthermore, since the compound represented by the formula (I) effectively inhibits TRPA1 activity, the compound can effectively mitigate unpleasant irritative sensation caused by TRPA1 activation. Accordingly, it can be seen that the compound represented by the formula (I) can be used as an active ingredient of an irritative sensation-mitigating agent for mitigating unpleasant irritative sensation caused by TRPA1 activation.

Test Example 2

The TRPM8-expressing cells obtained in Preparation Example 2 were incubated in a 10% by mass FBS-containing DMEM medium containing a reagent for measuring calcium ion in a cell, Fura 2-AM (manufactured by Invitrogen) at a final concentration of 5 μM at room temperature for 60 minutes, thereby introducing Fura 2-AM into the TRPM8-expressing cells, to obtain Fura 2-AM-introduced TRPM8-expressing cells.

The resulting Fura 2-AM-introduced TRPM8-expressing cells were put into each chamber of a fluorometric apparatus equipped with circulating thermostatic chambers [manufactured by Hamamatsu Photonics K.K. under the trade name of ARGUS-50]. Thereafter, the Fura 2-AM-introduced TRPM8-expressing cells in the chamber were washed with a solvent A [composition: 140 mM sodium chloride, 5 mM potassium chloride, 2 mM magnesium chloride, 2 mM calcium chloride, 10 mM glucose and 10 mM HEPES hydrochloric acid buffer (pH 7.4)]

Next, a test sample was put into the chamber containing the washed Fura 2-AM-introduced TRPM8-expressing cells, and the Fura 2-AM-introduced TRPM8-expressing cells and the test sample were mixed. As the test sample, there was used a TRPA1 activity-inhibitor (0.5 mM) which was prepared in the same manner as in Example 1 except that the concentration of 2-isobornyloxyethanol was adjusted to 0.5 mM or a sample (0.5 mM) which was prepared in the same manner as in Reference Example 1 except that the concentration of borneol was adjusted to 0.5 mM.

Thereafter, intensity of fluorescence E based on the Fura 2-AM introduced into the TRPM8-expressing cell and bound to a calcium ion in the cells at an excitation wavelength of 340 nm and intensity of fluorescence F based on the Fura 2-AM introduced into the TRAM8-expressing cell at an excitation wavelength of 380 nm were measured in the chamber.

Using the measured intensity of fluorescence E and F, $\Delta$fluorescence intensity ratio$_{test\ sample}$ was calculated on the basis of the formula (V). In the formula (V), the intensity of fluorescence E was used as fluorescence intensity$_{340\ nm}$, and the intensity of fluorescence F was used as fluorescence intensity$_{380\ nm}$. In the formula (V), the control is a solvent A.

Additionally, the same procedures as those of the case where the test sample was used were carried out except that a TRPM8 agonist was used alone in place of the test sample, and thereafter intensity of fluorescence G based on the Fura 2-AM introduced into the TRPM8-expressing cell at an excitation wavelength of 340 nm and bound to a calcium ion in the cell and intensity of fluorescence H based on the Fura 2-AM introduced into the TRPM8-expressing cell at an excitation wavelength of 380 nm were measured. As the agonist, a solvent A containing 1 mM menthol was used.

Using the measured intensity of fluorescence G and H, $\Delta$fluorescence intensity ratio$_{agonist}$ was calculated on the basis of the formula (IV). In the formula (IV), the intensity of fluorescence G was used as fluorescence intensity$_{340\ nm}$, and the intensity of fluorescence H was used as fluorescence intensity$_{380\ nm}$. In the formula (IV), the control is a solvent A.

Using the calculated $\Delta$fluorescence intensity ratio$_{test\ sample}$ and $\Delta$fluorescence intensity ratio$_{agonist}$, the ratio of TRPM8 activity enhanced by the test sample to TRPM8 activity enhanced by the agonist (hereinafter also referred to as "enhancement degree of TRPM8 activity") was calculated. Additionally, the enhancement degree of TRPM8 activity was calculated on the basis of the formula (VII):

Enhancement degree of TRPM8
activity=$\Delta$Fluorescence intensity ratio$_{test\ sample}$/
$\Delta$Fluorescence intensity ratio$_{agonist}$  (VII)

Figure 2:
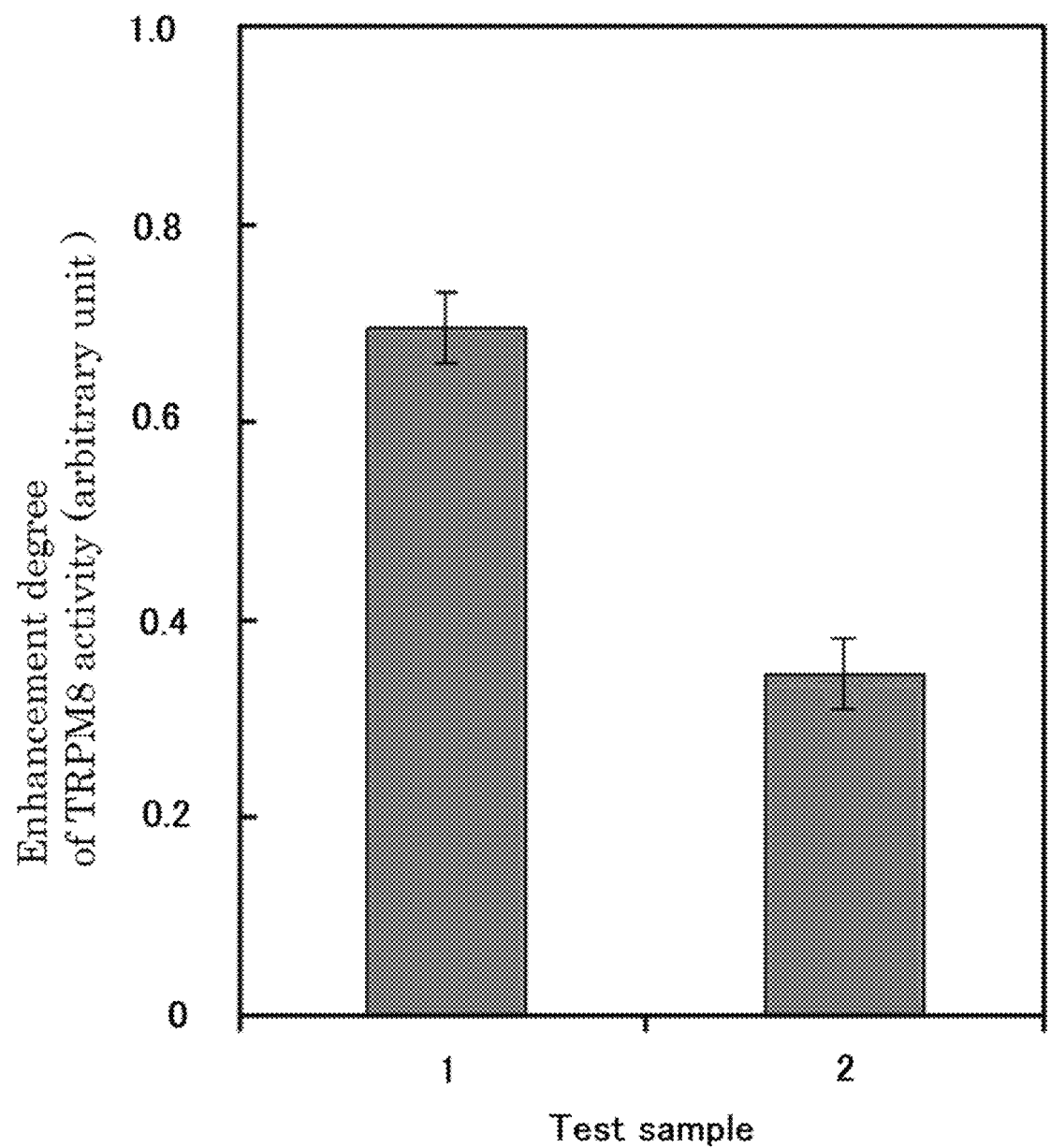
FIG. 2 is a graph showing results of examining the relationship between the kind of a test sample and the enhancement degree of TRPM8 activity in Test Example 2.

The results of examining relationship between the kind of the test sample and the enhancement degree of TRPM8 activity in Test Example 2 are shown in FIG. 2. In the figure, lane 1 shows the enhancement degree of TRPM8 activity in the case where the TRPA1 activity-inhibitor obtained in Example 1 as a test sample; and lane 2 shows the enhancement degree of TRPM8 activity in the case where the sample obtained in Reference Example 1 was used as a test sample.

From the results shown in FIG. 2, it can be seen that the enhancement degree of TRPM8 activity in the case where the TRPA1 activity-inhibitor obtained in Example 1 is used (see FIG. 2, lane 1) was about 0.69. On the other hand, it can be seen that the enhancement degree of TRPM8 activity in the case where the TRPA1 activity-inhibitor obtained in Reference Example 1 is used (see FIG. 2, lane 2) is about 0.35. From the results shown in FIGS. 1 and 2, it can be seen that 2-isobornyloxyethanol contained in the TRPA1 activity-inhibitor obtained in Example 1 has both a TRPA1 activity-inhibiting action and an action of enhancing TRPM8 activity which gives cold stimulation to skin (TRPM8 activity-enhancing action), and that 2-isobornyloxyethanol has the TRPM8 activity-enhancing action higher than that of borneol. Accordingly, from these results, it can be seen that the TRPA1 activity-inhibitor obtained in Example 1 exhibits an effect of suppressing unpleasant irritative sensation caused by TRPA1 activation and an effect of giving cold sensation to skin.

Examples 2, 3 and Comparative Examples 2 and 3

Ethanol, menthol, 2-isobornyloxyethanol and purified water were mixed so as to have a composition shown in Table 1, to obtain test external preparations of Examples 2, 3 and Comparative Examples 2 and 3.

Test Example 3

A part below the ear of the neck of a subject to whom the external preparation for skin would be applied was wiped with a wet towel, to remove sebum stain and the like. Next, the subject was allowed to rest in an evaluation room in which room temperature of 22±1° C. and humidity of 45±5% were maintained for 10 minutes. Thereafter, a nonwoven fabric [manufactured by Sanshoshigyo Co., Ltd, Product No.: KP9560, 3 cm long by 3 cm wide)] perfused with 750 µL of the test external preparation obtained in Example 2 was stuck on the part below the ear of the neck of the subject. Irritative sensation was evaluated by the subject at the elapsed time of 1, 3, 5, 7, and 10 minutes after sticking the non-woven fabric on the part below the ear of the neck of the subject. Additionally, the irritative sensation was evaluated by the subject in the same manner as in the above except that in the above, the test external preparations obtained in Example 3, Comparative Example 2 or Comparative Example 3 was used in place of the test external preparation obtained in Example 2. The irritative sensation was evaluated by using 5 items, stimulation of prickly feeling and tingling feeling, itching, burning sensation and discomfort with a focus on pain among evaluation items as the irritative sensation and scoring intensity scores of the irritative sensation in 6 grades of 0 to 5. Higher intensity score shows that the irritative sensation is stronger. The sum of the intensity scores at each elapsed time is shown in Table 1.

TABLE 1

|  | Example 2 | Comparative Example 2 | Example 3 | Comparative Example 3 |
| --- | --- | --- | --- | --- |
| Ethanol | 80 | 80 | 40 | 40 |
| Menthol | — | — | 0.5 | 0.5 |
| 2-Isobornyloxyethanol | 0.1 | — | 0.1 | — |
| Purified water | balance | balance | balance | balance |
| Total content (% by mass) | 100 | 100 | 100 | 100 |
| Sum of intensity scores | 2 | 3 | 17 | 21 |

From the results shown in Table 1, it can be seen that the total points of the intensity score of the stinging score (maximum value) in the case where ethanol (Example 2) or a mixture of menthol and ethanol (Example 3) was used together with 2-isobornyloxyethanol are lower than those in the case where ethanol (Comparative Example 2) or a mixture of menthol and ethanol (Comparative Example 3) was used without using 2-isobornyloxyethanol. Accordingly, from these results, it can be seen that an external preparation including the compound represented by the formula (I) such as 2-isobornyloxyethanol can suppress stimulation based on a component such as menthol and ethanol.

Examples 4, 5, Comparative Examples 4 and 5

Ethanol, menthol, a perfume, polyoxyethylene hardened castor oil (40) [addition number of moles of oxyethylene groups: 40], 2-isobornyloxyethanol, borneol and purified water are mixed so as to have in the composition shown in Table 2, to obtain test external preparations of Examples 4 and 5 and Comparative Examples 4 and 5.

Test Example 4

A vessel charged with the test external preparation obtained in Example 4 was left to stand in a booth for evaluating an aromatic agent for 20 minutes. Thereafter, preference of the aroma was evaluated by 15 panelists of evaluation specialists. Additionally, preference of the aroma was evaluated by 15 panelists of evaluation specialists in the same manner as in the above were carried out except that a vessel charged with the test external preparation obtained in Example 5, Comparative Example 4 or Comparative Example 5 was used in place of a vessel charged with the test external preparation obtained in Example 4. The preference was scored in 7 grades of −3 to 3 points. Higher points of preference indicate that "the panelists like the aroma of the external preparation for test", and lower points indicate that "the panelists dislike the aroma of the test external preparation". The average values of the points are shown in Table 2 as evaluation results of the preference.

Test Example 5

A vessel charged with the test external preparation obtained in Example 4 was left to stand in a booth for evaluating an aromatic agent for 20 minutes. Thereafter, level of comfort-discomfort of the aroma was evaluated by 15 panelists of evaluation specialists. Additionally, level of comfort-discomfort of the aroma was evaluated by 15 panelists of evaluation specialists in the same manner as that of the above except that a vessel charged with the external preparation for test obtained in Example 5, Comparative Example 4 or Comparative Example 5 was used in place of a vessel charged with the external preparation for test obtained in Example 4. Evaluation of the level of comfort-discomfort was carried out by scoring rank order of the 1st rank to the 4th rank (the 1st rank=comfort, the 4th rank=discomfort) for each external preparation for test. The level of comfort-discomfort is shown in Table 2 by the number of panelists of each rank order.

TABLE 2

|  | Example 4 | Example 5 | Comparative Example 4 | Comparative Example 5 |
| --- | --- | --- | --- | --- |
| Ethanol | 60 | 60 | 60 | 60 |
| Menthol | 0.05 | 0.05 | 0.05 | 0.05 |
| Perfume | 1 | 1 | 1 | 1 |
| Polyoxyethlene hydrogenated castor oil (40) | 3 | 3 | 3 | 3 |
| 2-Isobornyloxyethanol | 0.1 | 0.01 | — | — |
| Borneol | — | — | 0.1 | 0.01 |
| Purified water | balance | balance | balance | balance |
| Total content (% by mass) | 100 | 100 | 100 | 100 |
| Preference degree (mean value of points) | 0.467 | 0.867 | −1.133 | −0.067 |
| Level of comfort-discomfort | | | | |
| 1st rank | 7 | 6 | 1 | 1 |
| 2nd rank | 6 | 6 | 1 | 2 |
| 3rd rank | 1 | 2 | 1 | 10 |
| 4th rank | 1 | 1 | 12 | 1 |

From the results shown in Table 2, it can be seen that the preference degree (the average value of the points) in the case where 2-isobornyloxyethanol was used is higher than that in the case where borneol is used. Additionally, from the results of the level of comfort-discomfort, it can be seen that more panelists ranked the case where 2-isobornyloxyethanol is used as the 1st rank or the 2nd rank, as compared with the case where borneol is used. Accordingly, from these results, it can be seen that aroma of a perfume is not inhibited even in a case where an aromatic component is used in combination, since the compound represented by the formula (I) such as 2-isobornyloxyethanol generates a weak smell.

Formulation Example

Formulation Examples of the cosmetic of the present invention will be described below. Additionally, "E.O." in parentheses in the raw materials indicates an oxyethylene group. Furthermore, the number described before the "E.O." indicates the addition number of moles of oxyethylene groups.

Formulation Example 1 Skin Lotion

| | |
|---|---|
| 1,8-Cineol | 0.1% by mass |
| 2-Isobornyloxyethanol | 0.1% by mass |
| Polyoxyethylene hydrogenated castor oil (50E.O.) | 1.0% by mass |
| Glycerol | 1.5% by mass |
| 1,3-Butylene glycol | 15.0% by mass |
| Citric acid | 0.05% by mass |
| Sodium citrate | 0.1% by mass |
| 1,2-Octanediol | 0.2% by mass |
| Purified water | balance |
| Total content | 100.0% by mass |

Formulation Example 2 Deodorant Gel

| | |
|---|---|
| 2-Isobornyloxyethanol | 0.5% by mass |
| Menthol | 0.5% by mass |
| Acrylate/alkyl Methacrylate copolymer | 0.2% by mass |
| Potassium hydroxide | 0.02% by mass |
| Isononyl isononanate | 1.5% by mass |
| Triclosan | 0.1% by mass |
| Ethanol | 30.0% by mass |
| Perfume | appropriate amount |
| Purified water | balance |
| Total content | 100.0% by mass |

Formulation Example 3 Roll-on Deodorant Cosmetic

| | |
|---|---|
| 1,8-Cineol | 0.3% by mass |
| 2-Isobornyloxyethanol | 0.3% by mass |
| Menthol | 0.1% by mass |
| Triclosan | 0.1% by mass |
| Chlorohydroxyaluminum | 10.0% by mass |
| Isononyl isononanate | 1.0% by mass |
| Hydroxypropylcellulose | 1.0% by mass |
| Ethanol | 60.0% by mass |
| Perfume | appropriate amount |
| Purified water | balance |
| Total content | 100.0% by mass |

Formulation Example 4 Deodorant Spray

| | |
|---|---|
| (Composition of base material solution) | |
| Talc | 20.0% by mass |
| Silicic anhydride | 20.0% by mass |
| Chlorohydroxyaluminum | 10.0% by mass |
| 1,8-cineol | 0.5% by mass |
| 2-Isobornyloxyethanol | 0.5% by mass |
| Menthol | 1.5% by mass |
| Triclosan | 0.1% by mass |
| Dimethylpolysiloxane | 15.0% by mass |
| Perfume | appropriate amount |
| Isopropyl myristate | balance |
| (Composition of propellant) | |
| Liquefied petroleum gas(LPG) | 100.0% by mass |

Formulation Example 5 Deodorant Stick

| | |
|---|---|
| Isopropyl methylphenol | 0.2% by mass |
| Aluminum potassium sulfate | 20.0% by mass |
| Chlorohydroxyaluminum | 10.0% by mass |
| Stearyl alcohol | 5.0% by mass |
| Glyceryl monostearate | 3.0% by mass |
| Silicic anhydride | 35.0% by mass |
| Candelilla wax | 0.5% by mass |
| Castor oil | 0.1% by mass |
| 2-Isobornyloxyethanol | 0.5% by mass |
| Citral | 0.04% by mass |
| Eugenol | 0.05% by mass |
| Decamethylcyclopentasiloxane | balance |
| Total content | 100.0% by mass |

Formulation Example 6 Makeup Remover

| | |
|---|---|
| Polyoxyethylene glyceryl (caprylic acid/capric acid) ester | 3.0% by mass |
| Polyoxyethylene coconut oil fatty acid glyceryl ester | 2.0% by mass |
| N-[3-Alkyl(12,14)oxy-2-hydroxypropyl]-L-arginine hydrochloride | 0.2% by mass |
| 1,3-Butylene glycol | 5.0% by mass |
| 1,2-Octanediol | 0.1% by mass |
| 1,8-Cineol | 0.3% by mass |
| 2-Isobornyloxyethanol | 0.3% by mass |
| Sodium dihydrogenphosphate | appropriate amount |
| Disodium hydrogenphosphate | appropriate amount |
| Tocopherol acetate | appropriate amount |
| Phenoxy ethanol | appropriate amount |
| Purified water | balance |
| Total content | 100.0% by mass |

Formulation Example 7 Shower Gel

| | |
|---|---|
| Lauric acid | 5.0% by mass |
| Myristic acid | 7.0% by mass |
| Propylene glycol | 4.0% by mass |
| Betaine lauryldimethylaminoacetate | 3.5% by mass |
| Potassium hydroxide | 3.6% by mass |
| Sodium sulfite | 0.03% by mass |

-continued

| | |
|---|---|
| Methyl parahydroxybenzoate | 0.3% by mass |
| Phenoxy ethanol | 0.8% by mass |
| 2-Isobornyloxyethanol | 0.5% by mass |
| Edetate | appropriate amount |
| Perfume | appropriate amount |
| Purified water | balance |
| Total content | 100.0% by mass |

Formulation Example 8 Whitening Lotion

| | |
|---|---|
| 2-Isobornyloxyethanol | 0.1% by mass |
| Isopropyl methylphenol | 0.1% by mass |
| Menthol | 0.05% by mass |
| Polyoxyethylene hydrogenated castor oil(50E.O.) | 0.5% by mass |
| L-Ascorbic acid-2-glucoside | 1.0% by mass |
| Tranexamic acid | 1.0% by mass |
| Dibutylene glycol | 5.0% by mass |
| Citric acid | 0.05% by mass |
| Sodium citrate | 0.1% by mass |
| 1,2-Octanediol | 0.2% by mass |
| Purified water | balance |
| Total content | 100.0% by mass |

Formulation Example 9 Anti-Inflammatory Lotion

| | |
|---|---|
| 2-Isobornyloxyethanol | 0.1% by mass |
| Isopropyl methylphenol | 0.1% by mass |
| Menthol | 0.1% by mass |
| Ethanol | 5.0% by mass |
| Polyoxyethylene polyoxypropylene decyltetradecyl ether | 0.3% by mass |
| Dipotassium glycyrrhizinate | 0.1% by mass |
| Glycerol | 2.0% by mass |
| Dipropylene glycol | 3.0% by mass |
| Citric acid | 0.05% by mass |
| Sodium citrate | 0.1% by mass |
| 1,2-Octanediol | 0.2% by mass |
| Purified water | balance |
| Total content | 100.0% by mass |

Formulation Example 10 Medical Hair Growth Tonic

Base material solution having the following composition and propellant having the following composition are charged into a container so that mass ratio (base material solution/propellant) become 85/15, to obtain hair growth tonic used for a scalp care agent which is a quasi-drug.

(Base Material Solution)

| | |
|---|---|
| Ethanol | 50% by mass |
| Isopropyl methylphenol | 0.1% by mass |
| Menthol | 0.5% by mass |
| Nicotinamide | 0.1% by mass |
| 2-Isobornyloxyethanol | 0.5% by mass |
| PEG-50hydrogenated castor oil | 0.3% by mass |
| Panthenol | 0.3% by mass |
| Camphor | 0.1% by mass |
| Tocopherol acetate | 0.1% by mass |
| *Swertia japonica* liquid extract | 0.1% by mass |
| Purified water | balance |
| Total content of base material solution (Propellant) | 100.0% by mass |
| Dimethyl ether | 10% by mass |
| LPG | 90% by mass |
| Total content of propellant | 100.0% by mass |

Formulation Example 11 Face Mask

One gram of a non-woven fabric for a mask was impregnated with 4 g of a composition for a face mask having the following composition, to obtain a face mask.

(Composition for Face Mask)

| | |
|---|---|
| 2-Isobornyloxyethanol | 0.1% by mass |
| Polyoxyethylene hydrogenated castor oil (50E.O.) | 1.0% by mass |
| Dipropylene glycol | 5.0% by mass |
| Glycerol | 5.0% by mass |
| 1,3-Butylene glycol | 5.0% by mass |
| Citric acid | 0.05% by mass |
| Sodium citrate | 0.1% by mass |
| Sorbitol | 1.0% by mass |
| Ethanol | 1.0% by mass |
| Xanthane gum | 0.01% by mass |
| Sodium hyaluronate | 0.001% by mass |
| Hydrolyzed collagen | 0.001% by mass |
| Purified water | balance |
| Total content | 100.0% by mass |

Formulation Example 12 Face-Wash

| | |
|---|---|
| Lauric acid | 6.5% by mass |
| Myristic acid | 12.0% by mass |
| Stearic acid | 12.5% by mass |
| Glycerol | 10.0% by mass |
| Propylene glycol | 9.0% by mass |
| Polyethylene glycol 1500 | 8.0% by mass |
| Lauric acid amide propyl betaine | 0.4% by mass |
| Potassium hydroxide | 6.0% by mass |
| Menthol | 0.5% by mass |
| 2-Isobornyloxyethanol | 0.5% by mass |
| Perfume | 0.2% by mass |
| Purified water | balance |
| Total content | 100.0% by mass |

Formulation Example 13 Skin-Care Cream

| | |
|---|---|
| Liquid paraffin | 5.0% by mass |
| Paraffin | 5.0% by mass |
| Hydrogenated palm oil | 3.0% by mass |
| Behenyl alcohol | 3.0% by mass |
| Stearic acid | 1.0% by mass |
| Glyceryl tri (2-ethylhexanoate) | 5.0% by mass |
| Xanthane gum | 0.05% by mass |
| Carboxyvinyl polymer | 0.4% by mass |
| Polyoxyethylene sorbitan monostearate | 1.5% by mass |
| Glyceryl stearate | 0.5% by mass |

-continued

| | |
|---|---|
| 1,3-Butylene glycol | 10.0% by mass |
| 1,2 Octanediol | 0.2% by mass |
| 2-Isobornyloxyethanol | 0.3% by mass |
| glycerol mono-2-ethylhexyl ether | 0.35% by mass |
| Glycerol | 5.0% by mass |
| Potassium hydroxide | appropriate amount |
| Tocopherol | appropriate amount |
| Edetate disodium | appropriate amount |
| Perfume | appropriate amount |
| Purified water | balance |
| Total content | 100.0% by mass |

Formulation Example 14 Wiping Sheet Cosmetic

One gram of non-woven fabric was impregnated with 4 g of a wiping sheet composition having the following composition, to obtain a wiping sheet cosmetic.
(Wiping Sheet Composition)

| | |
|---|---|
| 2-Isobornyloxyethanol | 0.3% by mass |
| Menthol | 0.3% by mass |
| Talc | 10.0% by mass |
| Polyoxyethylene polyoxypropylene 2-decyltetradecyl ether | 0.2% by mass |
| Ethanol | 40.0% by mass |
| Perfume | appropriate amount |
| Purified water | balance |
| Total content | 100.0% by mass |

Formulation Example 15 Hair Dye

The following raw materials were mixed so as to have the following composition, to obtain a first agent for hair dye and a second agent for hair dye. When used, the first agent was mixed with the second agent so as to have mass ratio (first agent/second agent) of 80/20, to obtain a hair dye. Hereinafter, a percentage of each component means the percentage of each component in the hair dye (a mixture of the first agent and the second agent).
(First Agent)

| | |
|---|---|
| Cetyl alcohol | 5.0% by mass |
| Polyoxyethylene cetyl ether (20EO.) | 5.0% by mass |
| 1,3-Butylene glycol | 3.0% by mass |
| Monoethanol amine | 14.0% by mass |
| 2-Isobornyloxyethanol | 0.5% by mass |
| p-Aminophenol | appropriate amount |
| Resorcin | appropriate amount |
| Purified water | balance |
| Total content of the first agent | 80.0% by mass |

(Second Agent)

| | |
|---|---|
| 35% by volume of hydrogen peroxide | 9.0% by mass |
| Purified water | 11.0% by mass |
| Total content of the second agent (hair dye) | 20.0% by mass |
| Total content of the first agent and the second agent | 100.0% by mass |

Formulation Example 16 Skin Patch

Paste having the following composition was applied on a support, to obtain a skin patch.
(Paste)

| | |
|---|---|
| Polyacrylic acid | 5.0% by mass |
| Sodium polyacrylate | 2.0% by mass |
| Glycerol | 15.0% by mass |
| Polyoxyethylene hydrogenated castor oil | 0.7% by mass |
| Methyl salicylate | 0.2% by mass |
| Menthol | 0.5% by mass |
| 2-Isobornyloxyethanol | 0.5% by mass |
| Purified water | balance |
| Total content | 100.0% by mass |

The invention claimed is:

1. A composition, comprising a TRPA1 agonist and a therapeutically effective amount for inhibiting TRPA1 activity induced by the TRPA1 agonist of a compound represented by formula (I):

[Chem. 1]

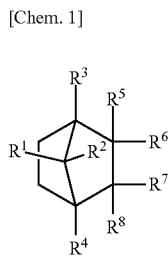

(I)

wherein each of $R^1$, $R^2$, $R^3$ and $R^4$ is independently a hydrogen atom or a methyl group, each of $R^5$, $R^6$, $R^7$ and $R^8$ is independently a hydrogen atom, a methyl group or a group represented by formula (II):

—O—$R^9$—OH    (II)

wherein $R^9$ is an alkylene group which may have a substituent;

with the proviso that at least one group of $R^5$, $R^6$, $R^7$ and $R^8$ is a group represented by the formula (II), and wherein the therapeutically effective amount of the compound represented by the formula (I) is able to inhibit the TRPA1 activity induced by the TRPA1 agonist.

2. The composition according to claim 1, wherein $R^9$ is an alkylene group having 1 to 6 carbons which may have a substituent, in the group represented by the formula (II).

3. The composition according to claim 1, which comprises a compound represented by formula (III):

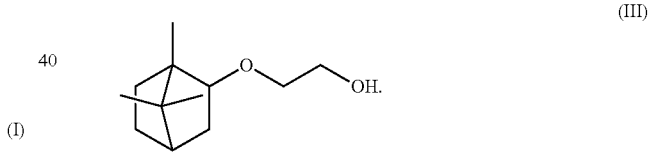

(III)

4. A method for inhibiting TRPA1 activity, comprising a step of applying a compound in a presence of a TRPA1 agonist to a skin which needs the inhibition of the TRPA1 activity induced by the TRPA1 agonist, thereby contacting a TRPA1-expressing cell in the skin with the compound, wherein the compound is represented by formula (I):

(I)

wherein each of $R^1$, $R^2$, $R^3$ and $R^4$ is independently hydrogen atom or methyl group, each of $R^5$, $R^6$, $R^7$ and $R^8$ is independently a hydrogen atom, a methyl group or a group represented by formula (II):

—O—$R^9$—OH    (II)

wherein $R^9$ is an alkylene group which may have a substituent;

with the proviso that at least one group of $R^5$, $R^6$, $R^7$ and $R^8$ is a group represented by the formula (II), and wherein the TRPA1 activity is exhibited by binding the TRPA1 agonist to TRPA1, thereby activating the TRPA1.

5. The method for inhibiting TRPA1 activity according to claim 4, wherein $R^9$ is an alkylene group having 1 to 6 carbons which may have a substituent, in the group represented by the formula (II).

6. The method for inhibiting TRPA1 activity according to claim 4, wherein the compound represented by the formula (I) is a compound represented by formula (III):

[Chem. 4]

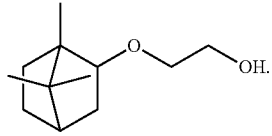

(III)

7. An external preparation containing a component for activating TRPA1, comprising the composition according to claim 1.

8. An irritative sensation-mitigating agent for mitigating irritative sensation caused by TRPA1 activation, which comprises the composition according to claim 1.

* * * * *